(12) United States Patent
Finkel et al.

(10) Patent No.: US 10,993,818 B2
(45) Date of Patent: May 4, 2021

(54) SYSTEM AND METHOD FOR SPINAL DISC REPLACEMENT SURGERY VIA A LATERAL APPROACH

(71) Applicant: AXIOMED, LLC, Malden, MA (US)

(72) Inventors: Joshua N. Finkel, Malden, MA (US); Alexander Bandazian, Malden, MA (US); Scott Foret, Malden, MA (US); Jeremy Crossgrove, Brookline, MA (US); Kingsley R. Chin, Wilton Manors, FL (US)

(73) Assignee: AXIOMED, LLC, Malden, MA (US)

( * ) Notice: Subject to any disclaimer, the term of this patent is extended or adjusted under 35 U.S.C. 154(b) by 239 days.

(21) Appl. No.: 15/984,550

(22) Filed: May 21, 2018

(65) Prior Publication Data

US 2018/0333277 A1 Nov. 22, 2018

Related U.S. Application Data

(60) Provisional application No. 62/509,348, filed on May 22, 2017.

(51) Int. Cl.
*A61F 2/46* (2006.01)
*A61B 17/16* (2006.01)
(Continued)

(52) U.S. Cl.
CPC ........ *A61F 2/4684* (2013.01); *A61B 17/1671* (2013.01); *A61B 17/1757* (2013.01); *A61F 2/30771* (2013.01); *A61F 2/442* (2013.01); *A61F 2/4611* (2013.01); *A61B 17/025* (2013.01); *A61B 17/1659* (2013.01); *A61B 17/1703* (2013.01); *A61B 17/846* (2013.01); *A61B 2017/0256* (2013.01); *A61B 2017/564* (2013.01); *A61B 2017/568* (2013.01); *A61F 2002/302* (2013.01); *A61F 2002/3023* (2013.01); *A61F 2002/30065* (2013.01); *A61F 2002/30125* (2013.01); *A61F 2002/30448* (2013.01); *A61F 2002/30563* (2013.01); *A61F 2002/30593* (2013.01); *A61F 2002/30772* (2013.01); *A61F 2002/30904* (2013.01); *A61F 2002/444* (2013.01); *A61F 2002/4615* (2013.01); *A61F 2002/4681* (2013.01);
(Continued)

(58) Field of Classification Search
CPC .............. A61F 2/4611; A61F 2/44–447; A61F 2002/4415–4495
See application file for complete search history.

(56) References Cited

U.S. PATENT DOCUMENTS 6,146,422 A 11/2000 Lawson
2004/0010316 A1* 1/2004 William ................ A61F 2/4425
623/17.16
(Continued)

OTHER PUBLICATIONS

ISR for PCT/US2018/033612, dated Aug. 9, 2018.

*Primary Examiner* — Matthew J Lawson
(74) *Attorney, Agent, or Firm* — AKC Patents LLC; Aliki K. Collins

(57) ABSTRACT

The present invention relates to a system and method for spinal disc replacement surgery via a lateral approach. The invention also relates to a spinal disc replacement device that is designed to be inserted via the lateral approach disc replacement surgery. The invention further relates to tools used for the spinal disc replacement surgery via the lateral approach.

10 Claims, 31 Drawing Sheets

(51) Int. Cl.
  *A61F 2/44* (2006.01)
  *A61B 17/17* (2006.01)
  *A61F 2/30* (2006.01)
  A61B 17/02 (2006.01)
  A61B 17/56 (2006.01)
  A61B 17/84 (2006.01)

(52) U.S. Cl.
  CPC ............ *A61F 2002/4687* (2013.01); *A61F 2310/00005* (2013.01)

(56) References Cited

U.S. PATENT DOCUMENTS

| | | |
|---|---|---|
| 2005/0027301 A1 | 2/2005 | Stihl |
| 2005/0131543 A1 | 6/2005 | Benzel et al. |
| 2006/0084986 A1 | 4/2006 | Grinberg et al. |
| 2007/0123985 A1* | 5/2007 | Errico .................. A61B 90/94 623/17.11 |
| 2010/0004657 A1* | 1/2010 | Dudasik ............ A61B 17/1757 606/96 |
| 2010/0249935 A1* | 9/2010 | Slivka .................. A61F 2/4611 623/17.16 |
| 2010/0292801 A1* | 11/2010 | Hansell ................ A61F 2/4684 623/17.16 |
| 2012/0010472 A1* | 1/2012 | Spann ...................... A61F 2/44 600/214 |
| 2012/0022651 A1* | 1/2012 | Akyuz ............... A61B 17/1757 623/17.16 |
| 2012/0088979 A1* | 4/2012 | Nunley ............. A61B 17/0206 600/231 |
| 2014/0350560 A1 | 11/2014 | Lee et al. |
| 2017/0304066 A1* | 10/2017 | Smith .................. A61F 2/4637 |

\* cited by examiner

SYSTEM AND METHOD FOR SPINAL DISC REPLACEMENT SURGERY VIA A LATERAL APPROACH

CROSS REFERENCE TO RELATED CO-PENDING APPLICATIONS

This application claims the benefit of U.S. provisional application Ser. No. 62/509,348 filed May 22, 2017 and entitled "SYSTEM AND METHOD FOR SPINAL DISC REPLACEMENT SURGERY VIA A LATERAL APPROACH", the contents of which are expressly incorporated herein by reference.

FIELD OF THE INVENTION

The present invention relates to a system and method for spinal disc replacement surgery and in particular to spinal disc replacement surgery via a lateral approach.

BACKGROUND OF THE INVENTION

Disorders of the spine occur when one or more of the individual vertebras and/or the intervertebral discs become abnormal either as a result of disease or injury. In cases where an intervertebral disc becomes abnormal, the degenerated intervertebral disc is usually surgically removed and replaced with an intervertebral implant device.

The common approach to the removal of a diseased intervertebral disc and replacement with an intervertebral implant is usually via a posterior or an anterior approach. Disc replacement surgery usually includes posterior laminectomy to first decompress the posterior neural elements and to gain access either through a direct posterior approach, or through a transpedicular approach, or through a posterior-lateral or transforaminal approach. After posterior exposure, the intervertebral disc is removed and replaced with an implant device inserted through a posterior-lateral approach or through a lateral transforaminal approach. Although open laminectomy provides exposure of the disc space, the large size of current implant devices often makes it technically challenging to avoid injury to the dura and nerve roots during insertion of the implant devices. The large exposure also puts the neural elements and spinal cord at risk from direct mechanical injury during insertion or scarring from overlying soft tissues postoperatively. Scarring is considered a major cause for failed back syndrome in which patients continue to have back and leg pain after spinal surgery. In order to avoid neural injuries with posterior implant devices some surgeons elect to approach the spine anteriorly, which allows for direct removal of intervertebral discs and vertebras without exposing the neural tissues. Vertebral bodies and intervertebral discs can also be removed anteriorly through a peritoneal or retro-peritoneal approach. Anterior approaches are now more popular and are becoming the standard approach for implanting intervertebral disc replacement devices but still require major surgery.

There is increasing consensus among surgeons that there is a need to develop devices, instruments, and methods to limit the size of the incision, extensive muscle stripping, prolonged retraction of muscles for visualization, avoidance of neural tissue retraction and injury, and denervation and devascularization that are known to contribute to poorer patient outcome after traditional open surgeries to treat pathologies deep within the body. In many cases these complications lead to permanent scarring and pain that can be more severe than the pain from the initial ailment. Limiting these complications in addition to the operative, general anesthesia, and recovery times are among the goals of this invention and that of percutaneous or minimally invasive surgeries.

This invention addresses the need for spinal disc replacement surgery that adheres to the principals of the less exposure surgery (LES) of outpatient surgery, which include minimizing the size of the incision, minimizing extensive muscle stripping, minimizing prolonged retraction of muscles for visualization, and preventing neural tissue retraction and injury.

Current disc replacement devices are fixed in size and shape and although techniques are now being developed to insert these devices percutaneously, for example U.S. Pat. Nos. 5,792,044 and 5,902,231 attributed to Foley et al., the fixed size and shapes of these interbody devices still require distraction instrumentation and techniques to access the intervertebral disc space which necessitates open surgery for anterior placements and limited open exposures for posterior procedures. The majority of these disc replacement devices are designed based on a ball-and-socket articulating principle with variable degrees of motion in different planes from a constrained device limiting some motion to a fully unconstrained device with motion in all planes. However, these devices do not permit percutaneous access primarily because they are fixed in shape and size, need to be inserted as separate articulating components, require distraction instrumentation and techniques to open the disc space, and they need to be anchored to the vertebral endplate.

Accordingly, there is a need for an intervertebral implant device that can be inserted via minimally invasive surgery (MIS) and can maintain spinal mobility.

SUMMARY OF THE INVENTION

The present invention relates to a system and method for spinal disc replacement surgery and in particular to spinal disc replacement surgery via a lateral approach. The invention also relates to a spinal disc replacement device that is designed to be inserted via a lateral approach disc replacement surgery.

In general in one aspect, the invention features a method for spinal disc replacement including the following. First, making an incision along a lateral direction of a patient's abdominal oblique muscles to access an intervertebral disc located between adjacent superior and inferior vertebras via a lateral approach. Next, making an incision through an annulus fibrosis of the intervertebral disc and removing a nucleus pulposus of the intervertebral disc to generate an opened disc space. Next, determining and selecting an appropriate sized and shaped implant for the opened disc space by inserting incremental trial implants into the opened disc space, wherein the trial implants comprise varying footprint sizes, wedge angle and height. Next, determining a trial implant depth so that in anterior-posterior X-ray imaging views first and second reference circles on first and second sides of the trial implants are aligned, respectively. Next, generating first and second openings located on the superior and inferior vertebras, respectively, by using a guide tool comprising a rod and a plate mounted at a distal end of the rod and wherein the plate comprises first and second reference openings, and drilling into the superior and inferior vertebras through the first and second reference openings and wherein the first and second openings comprise depths selected based on the patient's anatomy. Next, inserting first and second Steinmann pins into the first and second openings, respectively. Next, inserting a tooth profile cutter in the opened disc space between the first and second Steinmann pins by mounting the tooth profile cutter to the plate of the guide tool and inserting the first and second reference openings of the plate over the first and second Steinmann pins and then cutting first and second tooth profiles in the inferior and superior surfaces of the superior and inferior vertebras, respectively, and wherein the first and second tooth profiles correspond to tooth profiles on top and bottom surfaces of a selected implant, respectively. Next, removing the tooth profile cutter from the opened disc space and inserting the selected implant in the disc space between the first and second Steinmann pins by mounting the selected implant to the plate of the guide tool and inserting the first and second reference openings of the plate over the first and second Steinmann pins.

Implementations of this aspect of the invention may include one or more of the following features. The may further include placing the patient in a lateral decubitus position on an operating table prior to making the incision. The may further include using a rasp to prepare an inferior endplate of the superior vertebra and a superior endplate of the inferior vertebra. The may further include removing any bone spurs or osteophytes from the opened disc space and the inferior endplate of the superior vertebra and the superior endplate of the inferior vertebra. The tooth profile cutter is inserted at a depth determined so that in anterior-posterior X-ray imaging views first and second reference circles on first and second sides of the tooth profile cutter are aligned, respectively. The may further include passing an inserter over the first and second Steinmann pins, securing the inserter to the Steinmann pins, connecting the selected implant to an advancing section of the inserter and inserting the selected implant into the opened disc space by advancing the advancing section of the inserter. The may further include distracting the opened disc space equally bilaterally with a parallel distractor tool. The tooth profile cutter comprises a half rail cutter. The may further include after inserting the half rail cutter into the opened disc space, removing the half rail cutter and inserting a full rail cutter that corresponds to the half rail cutter.

In general in another aspect the invention features a method for spinal disc replacement including the following. First, making an incision along a lateral direction of a patient's abdominal oblique muscles to access an intervertebral disc located between adjacent superior and inferior vertebras via a lateral approach. Next, making an incision through an annulus fibrosis of the intervertebral disc and removing a nucleus pulposus of the intervertebral disc to generate an opened disc space. Next, inserting a centering broach tool in the opened disc space, wherein the centering broach tool comprises an elongated shaft and a broach mounted at a distal end of the elongated shaft and wherein a proximal end of the broach comprises a stop endplate and the elongated shaft comprises first and second alignment pins that are used to establish a lateral center, and wherein the broach is entered in the opened disc space until the stop endplate stops against sides of the superior and inferior vertebras. Next, generating first and second openings located on the superior and inferior vertebras, respectively, by using a drill guide tool, wherein the drill guide tool comprises an elongated tubular component configured to slide over the elongated shaft of the broach and first and second tubular drill guides surrounding a distal end of the elongated tubular component and drilling into the superior and inferior vertebras through the first and second tubular drill guides and wherein the first and second openings comprise depths selected based on the patient's anatomy, as viewed under fluoroscopic imaging. Next, inserting first and second Steinmann pins into the first and second openings, respectively. Next, determining and selecting an appropriate sized and shaped implant for the opened disc space by inserting incremental trial implants into the opened disc space between the first and second Steinmann pins by mounting the trial implant to an end of the elongated tubular component of the drill guide tool and inserting the first and second tubular drill guides over the first and second Steinmann pins, wherein the trial implants comprise varying footprint sizes, wedge angle and height. Next, determining a trial implant depth so that in anterior-posterior X-ray imaging views an opening at a side of the trial implants is centered, respectively. Next, inserting a tooth profile cutter in the opened disc space between the first and second Steinmann pins by mounting the tooth profile cutter to an end of the elongated tubular component of the drill guide tool and inserting the first and second tubular drill guides over the first and second Steinmann pins and then cutting first and second tooth profiles in the inferior and superior surfaces of the superior and inferior vertebras, respectively, and wherein the first and second tooth profiles correspond to tooth profiles on top and bottom surfaces of a selected implant, respectively. Next, removing the tooth profile cutter from the opened disc space and inserting the selected implant in the disc space between the first and second Steinmann pins by mounting the selected implant to an end of the elongated tubular component of the drill guide tool and inserting the first and second tubular drill guides over the first and second Steinmann pins.

In general in another aspect the invention features a centering broach tool including an elongated shaft and a broach mounted at a distal end of the elongated shaft. A proximal end of the broach comprises a stop endplate and the elongated shaft comprises a connect feature at a proximal end and first and second alignment pins that are used to establish a lateral center.

Implementations of this aspect of the invention may include one or more of the following features. The connect feature comprises one of cylindrical, spherical, or polygonal profile. The broach comprises an elongated parallelepiped with a triangular shaped cutting distal end. The stop endplate comprises one or more fingers extending from a top surface and/or a bottom surface of the stop endplate; and wherein the fingers are used for measuring a lateral center of an insertion site for the centering broach. The centering broach tool further includes a Steinmann pin guide tool comprising an elongated tubular shaft, first and second tubular components and a stop plate and wherein the elongated tubular shaft is configured to slide over the elongated shaft of the centering broach too, wherein the stop plate extends from a distal end of the elongated tubular shaft and the first and second tubular components connect to the stop plate by engaging a ball detent feature with a corresponding feature on the stop plate and wherein a locking tooth formed in each of the tubular components engages a space between the fingers of the stop endplate of the centering broach tool.

In general in another aspect the invention features an implant insertion tool including an elongate shaft and a Steinmann pin interface component. The Steinmann pin interface component comprises a central opening and first and second tubular components configured to pass over first and second Steinmann pins. The elongated shaft is configured to pass through the central opening of the Steinmann pin interface component and comprises a distal end configured to attach to an implant.

In general in another aspect the invention features an artificial disc to replace a damaged spinal disc in a spinal column. The artificial disc includes a first plate having an outer side engagable with a first vertebra of the spinal column and an inner side, a second plate having an outer side engagable with a second vertebra of the spinal column and an inner side and a resilient core disposed between the first and second plates, and the resilient core is fixedly connected to the inner sides of the first and second plates and comprises urethane silicon blend material.

Implementations of this aspect of the invention may include one or more of the following features. The first and second plates are made of polymeric materials. The first and second plates are elongated oval-shaped and domed or bowed to fit the first and second vertebras, respectively. The first and second plates comprise first and second recesses formed in apexes of peripheral rims of the oval-shaped plates, respectively, for engagement by an implant insertion tool.

BRIEF DESCRIPTION OF THE DRAWINGS

Referring to the figures, wherein like numerals represent like parts throughout the several views.

DETAILED DESCRIPTION OF THE INVENTION

The present invention relates to a system and method for spinal disc replacement surgery via a lateral approach. The invention also relates to a spinal disc replacement device that is designed to be inserted via a lateral approach disc replacement surgery.

Figure 1A:
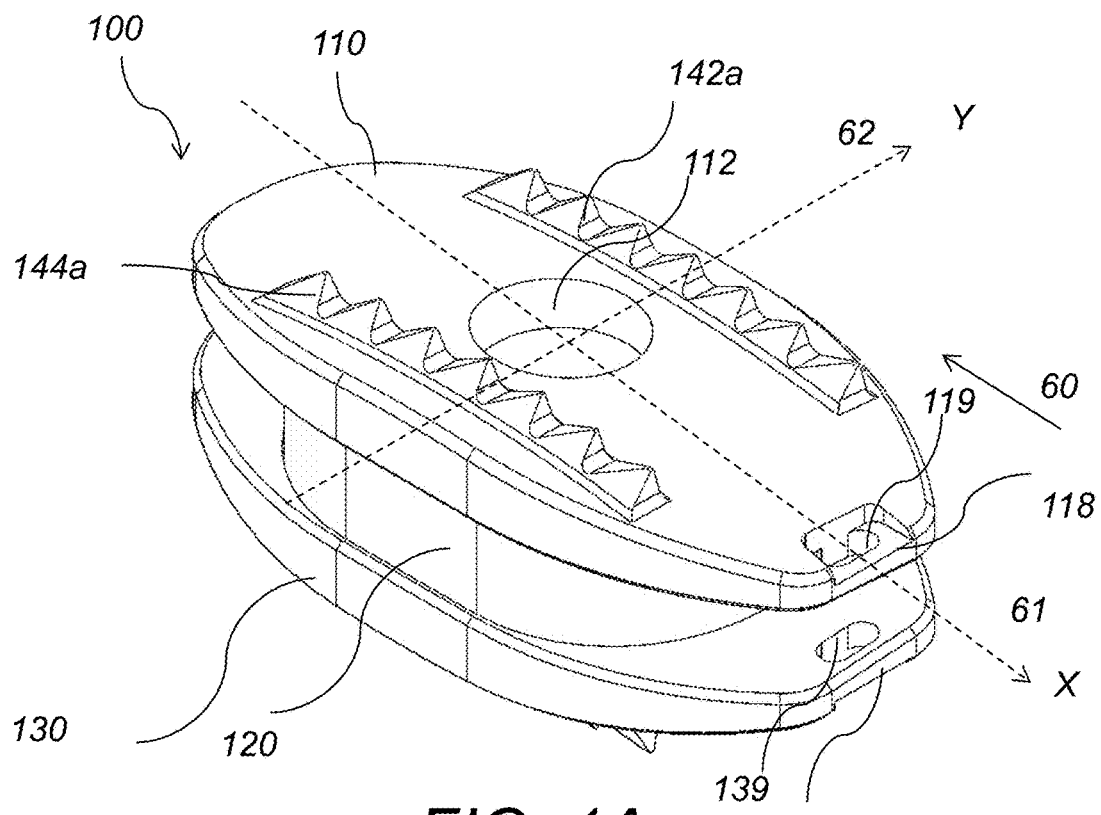
FIG. 1A depicts a perspective view of a spinal disc replacement device that is designed to be inserted via a lateral approach surgery.
Figure 1B:
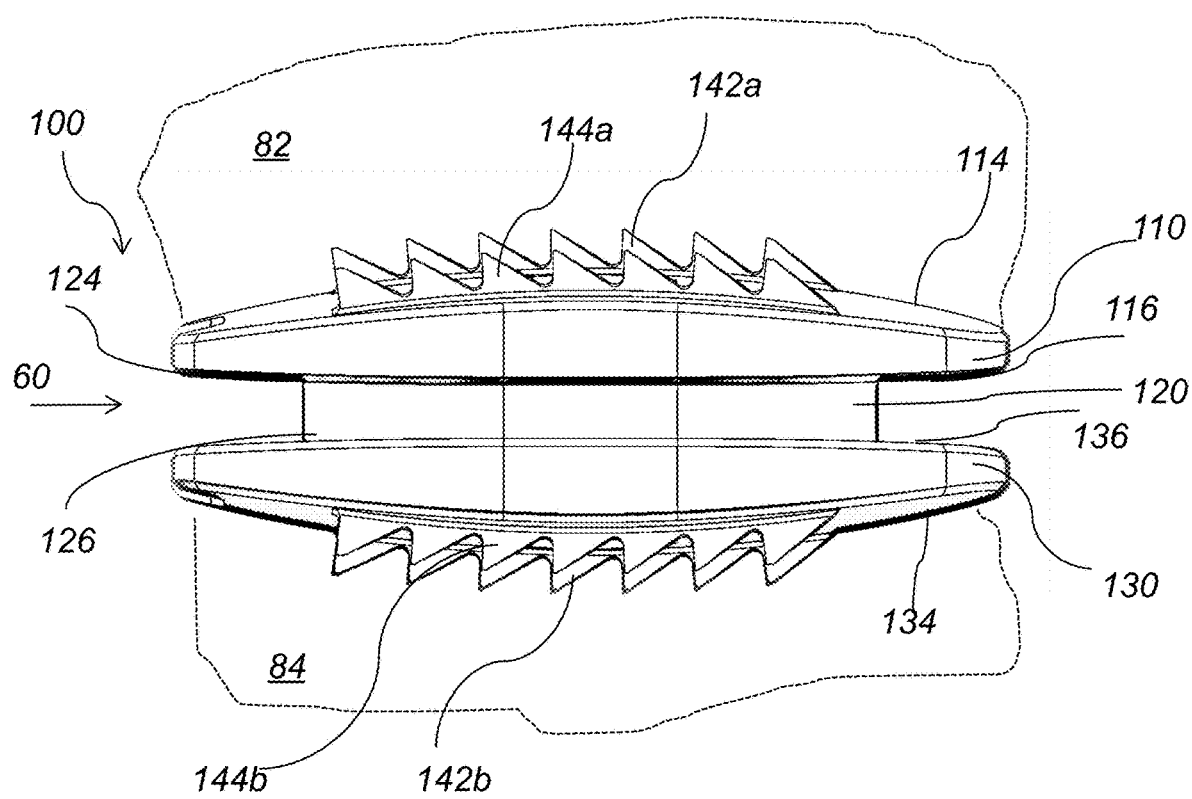
FIG. 1B depicts a front view of the disc replacement device of FIG. 1A.
Figure 1C:
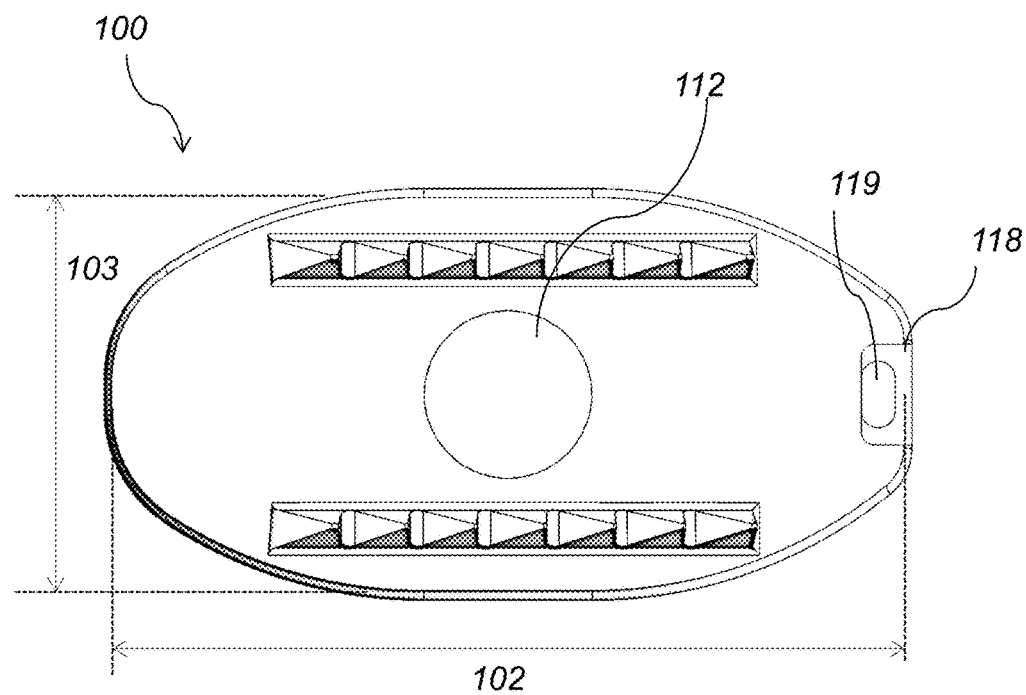
FIG. 1C depicts a top view of the disc replacement device of FIG. 1A.
Figure 6A:
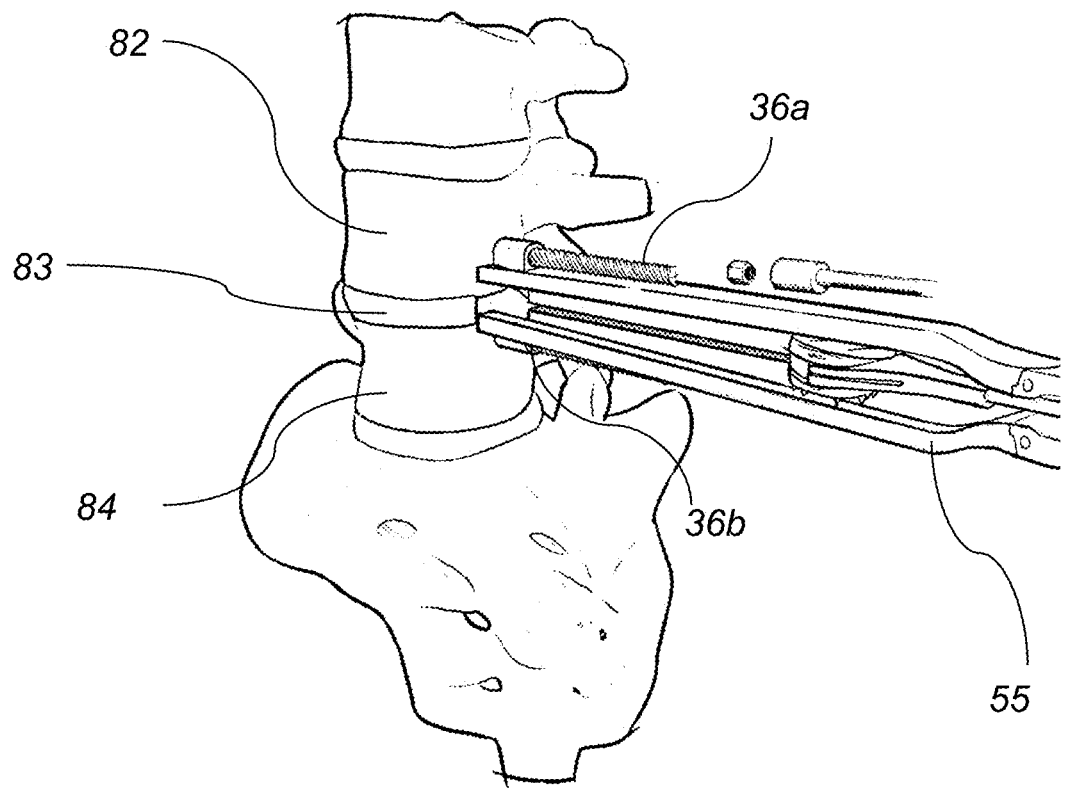
FIG. 6A to FIG. 6C are schematic diagrams of the steps of another embodiment of the spinal disc replacement surgery via a lateral approach, according to this invention.
Figure 6B:
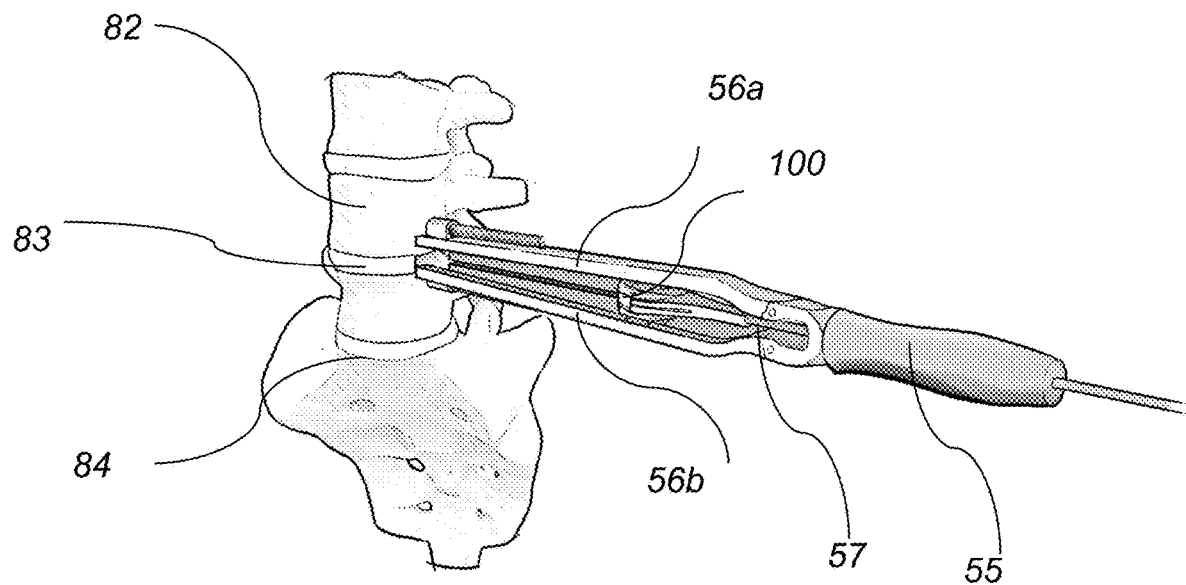
Figure 6C:
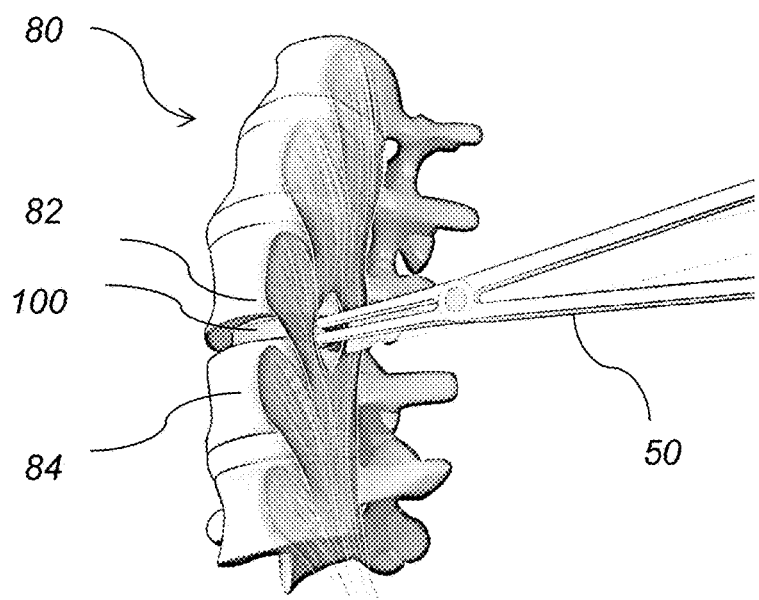

Referring to FIG. 6C and FIG. 1B, a spinal disc replacement device 100 replaces a damaged or degenerated disc in a spinal column 80 of a patient. The spinal disc replacement device 100 is disposed between upper and lower vertebrae 82 and 84 of a spinal column 80. Although the spinal disc replacement device 100 is particularly advantageous for replacement of a damaged spinal disc in a lumbar portion of the spinal column 80, the spinal disc replacement device 100 may be utilized to replace a damaged disc in the cervical portion of a patient's spinal column.

Figure 1D:
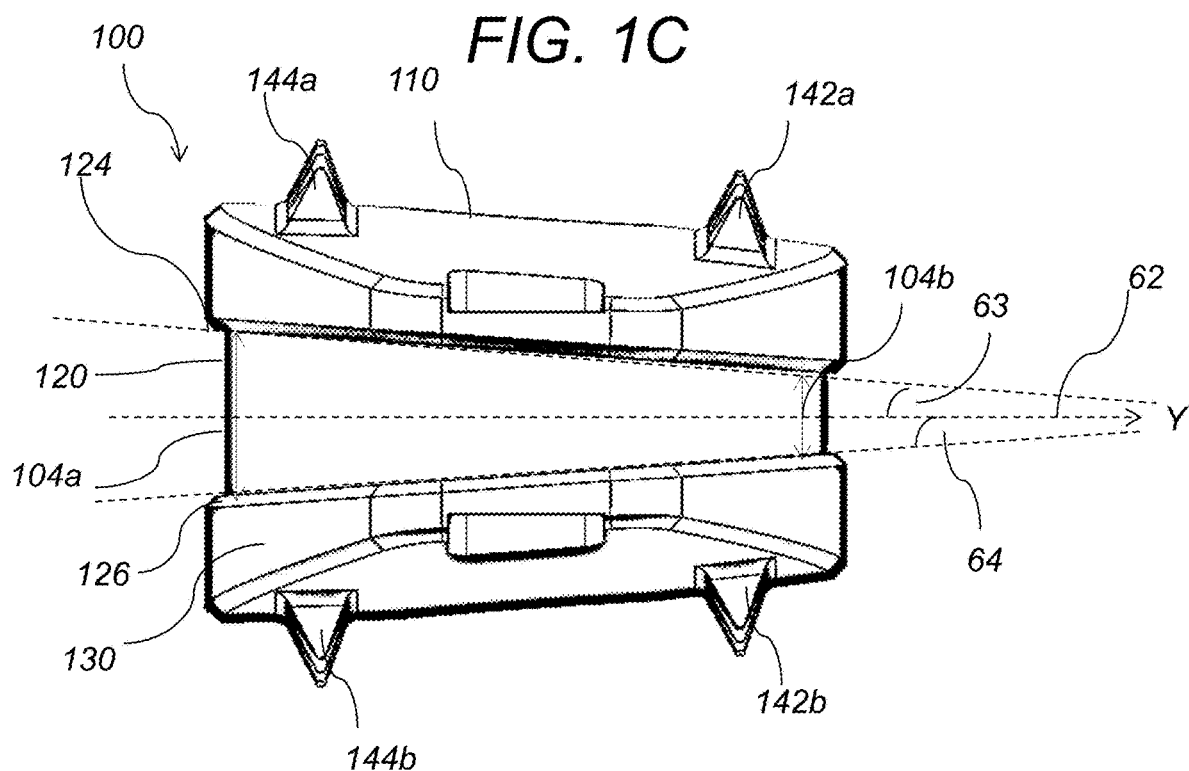
FIG. 1D depicts a lateral (side) view of the disc replacement device of FIG. 1A.
Figure 2A:
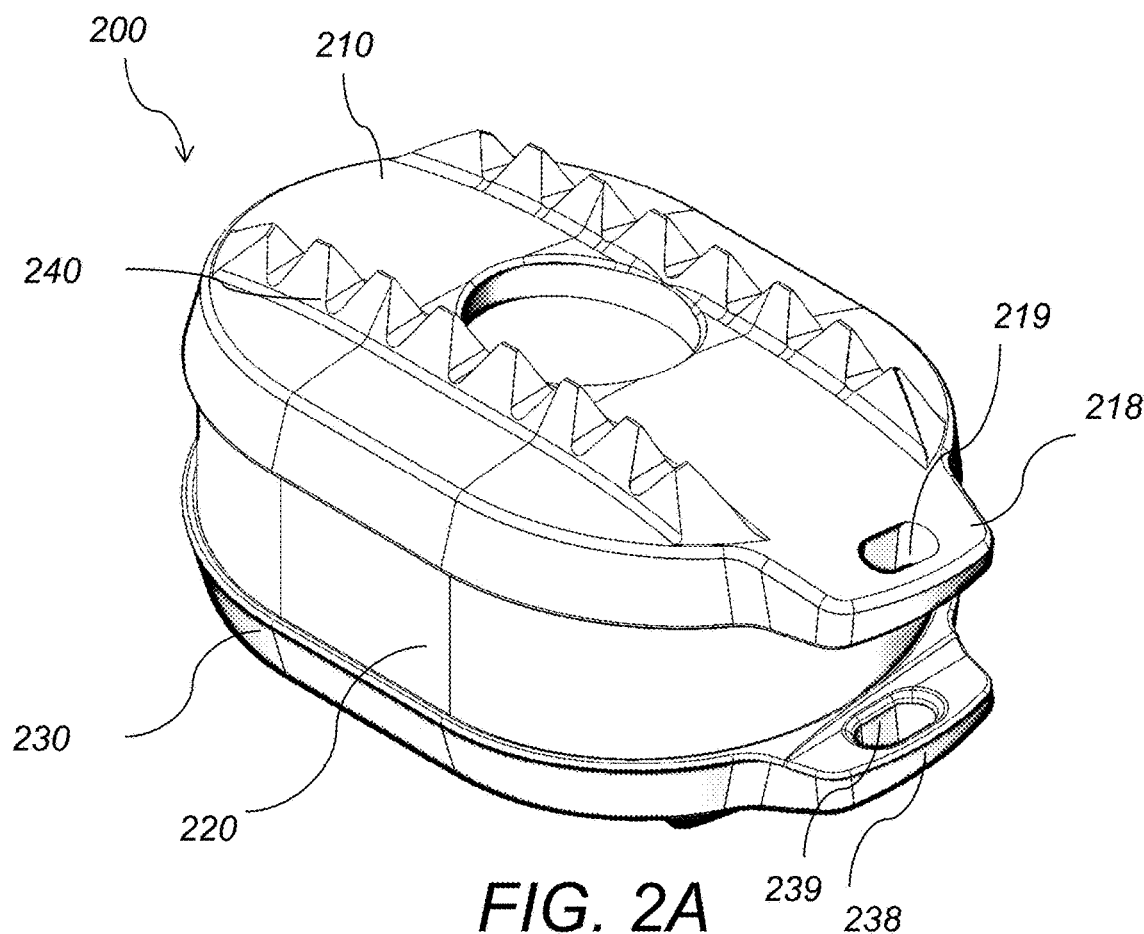
FIG. 2A depicts a perspective view of another embodiment of a spinal disc replacement device that is designed to be inserted via a lateral approach surgery.
Figure 2B:
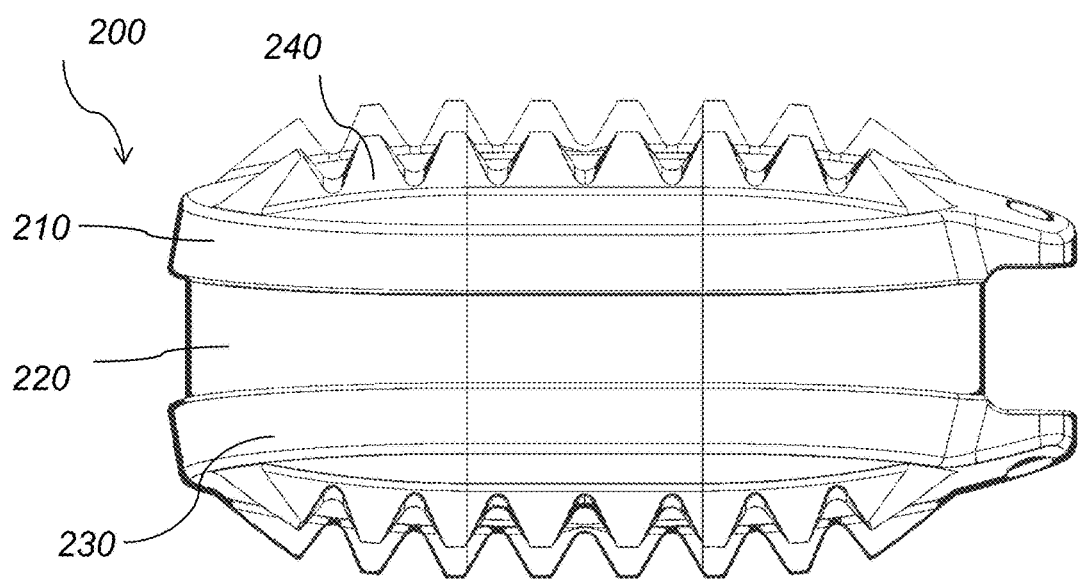
FIG. 2B depicts a front view of the disc replacement device of FIG. 2A.
Figure 2C:
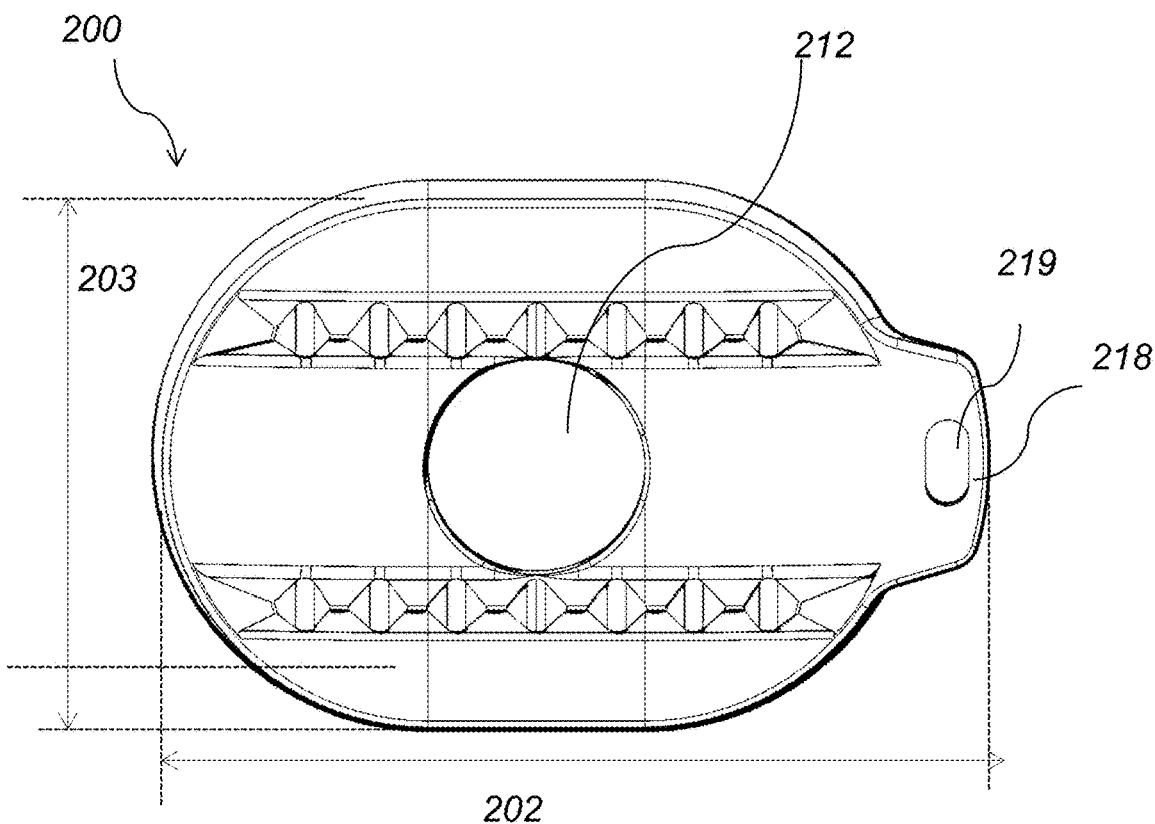
FIG. 2C depicts a top view of the disc replacement device of FIG. 2A.
Figure 2D:
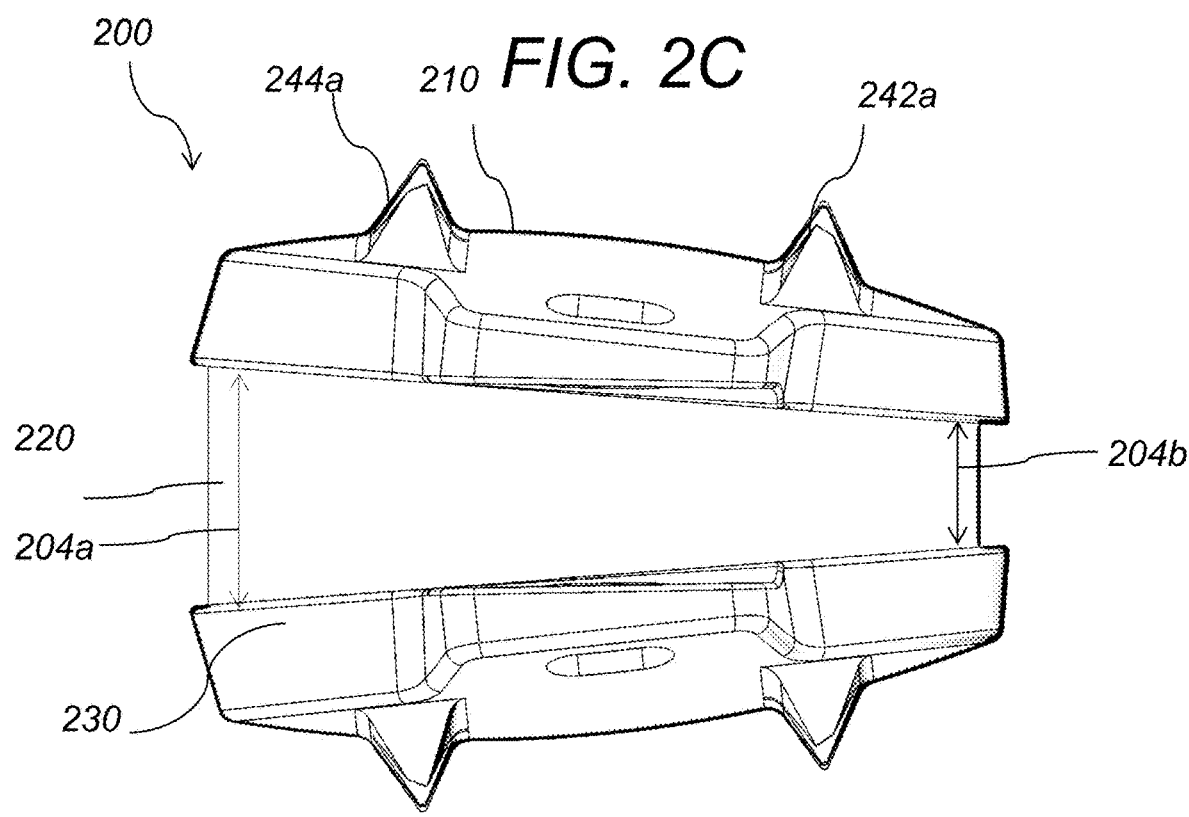
FIG. 2D depicts a lateral (side) view of the disc replacement device of FIG. 2A.

Referring to FIG. 1A-FIG. 1D, the spinal disc replacement device 100 includes upper and lower plates 110, 130 and a resilient core or central section 120 formed of a polymeric material. The resilient core 120 is made of a urethane silicon blend. However, it is contemplated that the resilient core 120 may be formed of different materials if desired. Core 120 is illustrated in FIG. 1A as being formed of a solid piece of material. In other embodiments, core 120 has a cylindrical central opening or passage. It is contemplated that the passage in the core may have any desired shape and not extend through the core 120 so that it defines a recess. In this embodiment, the upper surface 124 and the lower surface 126 of the core 120 are inclined and form angles 63 and 64 with the major Y-axis 62, respectively, as shown in FIG. 1D. Angles 63 and 64 may be in the range of zero to 60 degrees.

Upper and lower plates 110 and 130 are fixedly connected to opposite sides 124 and 126 of the core 120. The upper and lower plates 110 and 130 are prevented from sliding or moving relative to the upper and lower surfaces 124, 126 of the core 120. The upper and lower plates 110 and 130 are formed of metal, specifically titanium. However, the upper and lower plates 110 and 130 may be formed of other biocompatible materials. For example, the upper and lower plates 110 and 130 may be formed of a polymeric material.

The upper plate 110 engages the upper vertebra 82, as shown in FIG. 1B. Similarly, the lower plate 130 engages the lower vertebra 84. Although the upper and lower plates 110 and 130 have the same construction, they may have different constructions if desired.

It is contemplated that the upper and lower plates 110 and 130 may be provided with features to resist expulsion of the spinal disc replacement device 100 from between the upper and lower vertebrae 82 and 84. The features which resist expulsion of the spinal disc replacement device 100 from between the upper and lower vertebrae 82 and 84 may be teeth, fins, screws, plates, or ridges. The features which resist expulsion of the spinal disc replacement device 100 from between the vertebrae 82 and 84 may be integrally formed as one piece with the upper and lower plates 110 and 130. Alternatively, the features which resist expulsion of the spinal disc replacement device 100 from between the vertebrae 82 and 84 may be formed separately from the upper and lower plates 110 and 130 and connected to the upper and lower plates. Illustrative examples of some of the many features which may be used to resist expulsion of the spinal disc replacement device 100 from between the upper and lower vertebrae 82 and 84 are illustrated in U.S. Pat. Nos. 5,534,030; 6,607,558; and 7,128,761, and U.S. Patent Publication No. US 2014/0316524, the contents of which are incorporated herein by reference in their entirety.

The identical upper and lower plates 110 and 130 are domed or bowed to fit the upper and lower vertebrae 82 and 84, respectively, to further resist expulsion. However, the upper and lower plates 110 and 130 may have a generally flat construction. If desired, the upper and lower plates 110 and 130 may have a coating or surface treatment on the bone-interface side to promote bony ingrowth into the plates.

The illustrated upper and lower plates 110 and 130 have circular central openings 112 and 132 (not shown). Openings 112 and 132 may be axially aligned with a cylindrical opening or passage through the resilient core 120. If desired, the openings 112 and 132 in the upper and lower plates 110 and 130 may be omitted or may receive members to close the openings. Alternatively, the openings 112 and 132 in the upper and lower plates 110 and 130 may have a configuration other than the illustrated circular configuration. Similarly, the cylindrical opening through the resilient core 120 may be eliminated or may have a configuration other than the illustrated cylindrical configuration.

Each of the upper and lower plates 110, 130 has a generally oval configuration extending along the major X-axis 61. The outer side 114 of the upper plate 110, is domed to fit the anatomy of the upper vertebrae 82 and to resist expulsion of the spinal disc replacement device 100 from between the upper and lower vertebrae 82 and 84. In this embodiment, the inner side 116 of the upper plate 110 is curved and inclined to match the curvature of the upper side 124 of the core 120. In other embodiments, the inner side 116 of the upper plate 110 is flat to match the upper side 124 of the core 120. The center of curvature of the inner side 116 may, if desired, be offset from the center of curvature of the outer side 114.

Similarly, the outer side 134 of the lower plate 130, is bowed to fit the anatomy of the lower vertebrae 84 and to resist expulsion of the spinal disc replacement device 100 from between the upper and lower vertebrae 82 and 84. In this embodiment, the inner side 136 of the lower plate 130 is curved and inclined to match the curvature of the lower side 126 of the core 120. In other embodiments, the inner side 136 of the lower plate 130 is flat to match the flat surface of the lower side 126 of the core 120. The center of curvature of the inner side 136 may, if desired, be offset from the center of curvature of the outer side 134.

In the embodiment of FIG. 1A-FIG. 1D, the outer side 114 of the upper plate 110 has teeth-shaped features 140 arranged in two parallel rows 142a, 144a that extend along the major axis 61 of the oval shaped upper plate 110. Similarly, the outer side 134 of the lower plate 130 has teeth-shaped features 140 arranged in two parallel rows 142b, 144b that extend along the major axis 61 of the oval shaped lower plate 130. In this embodiment, teeth 140 are inclined toward a direction opposite the implant insertion direction 60, as shown in FIG. 1B. In other embodiments, each of the outer sides 114 and 134 includes more than two rows of teeth-shaped features 140.

The polymeric material of the resilient core 120 is fixedly bonded to the inner sides 116, 136 of the upper and lower plates 110, 130, respectively. This bonding may be effected by molding the core to the plates 110, 130. It is contemplated that the bonding may be effected by heating or otherwise softening the material on the upper and lower sides of the resilient core 120 and pressing the softened sides of the resilient core firmly against the inner sides 116, 136 of the upper and lower plates 110, 130, respectively. If desired, an adhesive may be used to fixedly interconnect the resilient core 120 and the inner sides 116, 136 of the upper and lower plates 110, 130, respectively.

In this embodiment of FIG. 1A-FIG. 1D, upper and lower plates 110, 130 are longer than the length of the resilient core and extend over the front and back of the core. In other embodiments, upper and lower plates 110, 130 have about the same length as the resilient core and do not extend over the front and back of the core, as will be described below. In yet other embodiments, upper and lower plates 110, 130 are wider than the width of the resilient core 120 and extend over the left and right sides of the core. In one example, upper and lower plates 110, 130, have a length 102 in the range of 30 mm to 70 mm, a width 103 in the range of 10 mm to 40 mm, and a thickness in the range of 1 mm to 10 mm. The resilient core 120 may have a length in the range of 30 mm to 70 mm, a width in the range of 10 mm to 40 mm, and a thickness in the range of 6 mm to 22 mm. In one example, the thickness 104a of the resilient core in the left side of the core is in the range of 6 mm to 22 mm and the thickness 104b of the resilient core on the right side of the core is in the range of 6 mm to 22 mm.

To facilitate positioning of the spinal disc replacement device 100 between the upper and lower vertebrae 82, 84, recesses 118 and 138 are formed in the apexes of the peripheral rims of the elongated oval-shaped upper and lower plates 110, 130, respectively. Openings 119 and 139 are provided in the recesses 118 and 138, respectively, for engagement by an insertion tool. The insertion tool has the same construction as is disclosed in U.S. Pat. No. 7,128,761. However, it should be understood that insertion tools having a different construction may be utilized to insert the spinal disc replacement device 100 between the upper and lower vertebrae 82 and 84.

Referring to FIG. 2A-FIG. 2D, in another embodiment, the spinal disc replacement device 200, includes upper and lower plates 210, 230 and a resilient core or central section 220 formed of a polymeric material. In this embodiment, upper and lower plates 210, 230 have about the same length and the same width as the core 220. In one example, upper and lower plates have a length 202 in the range of 30 mm to 70 mm, a width 203 in the range of 10 mm to 40 mm, and a thickness in the range of 1 mm to 10 mm. The resilient core 220 may have a length in the range of 30 mm to 70 mm, a width in the range of 10 mm to 40 mm, and a thickness in the range of 6 mm to 22 mm. In one example, the thickness 204a of the resilient core in the left side of the core is in the range of 6 mm to 22 mm and the thickness 204b of the resilient core on the right side of the core is in the range of 6 mm to 22 mm. In this embodiment, teeth 240 formed on the top surfaces of the upper and lower plates 210, 230 are not inclined. Furthermore, tabs 218 and 238 extend from one of the two apexes of the peripheral rims of each of the elongated oval-shaped upper and lower plates 210, 230, respectively. Openings 219 and 239 are provided in the tabs 218 and 238, respectively, for engagement by an insertion tool. In other embodiments, tabs extend from both apexes of the peripheral rims of each of the elongated oval-shaped upper and lower plates 210, 230.

Figure 3:
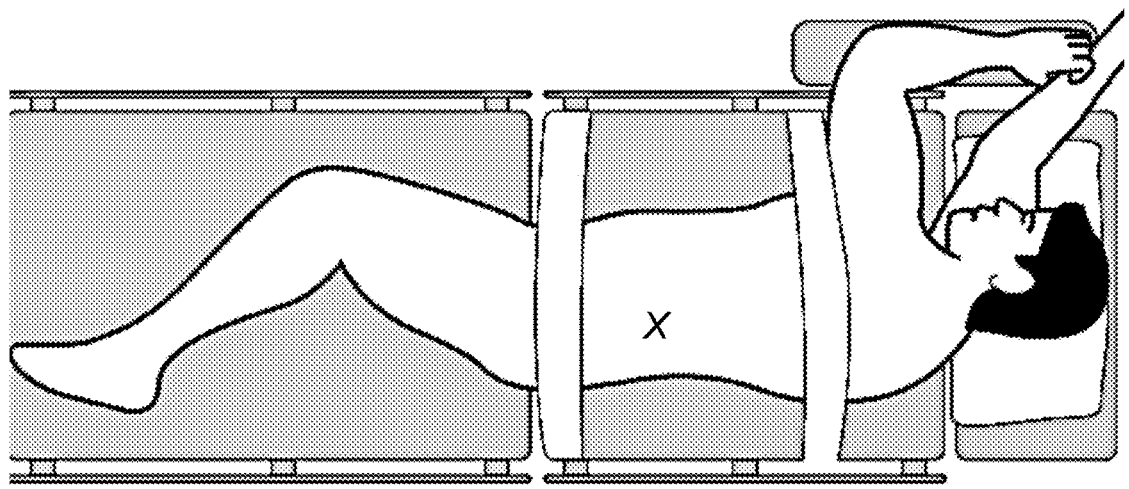
FIG. 3 depicts the position of the patient during spinal disc replacement surgery via a lateral approach, according to this invention.
Figure 4:
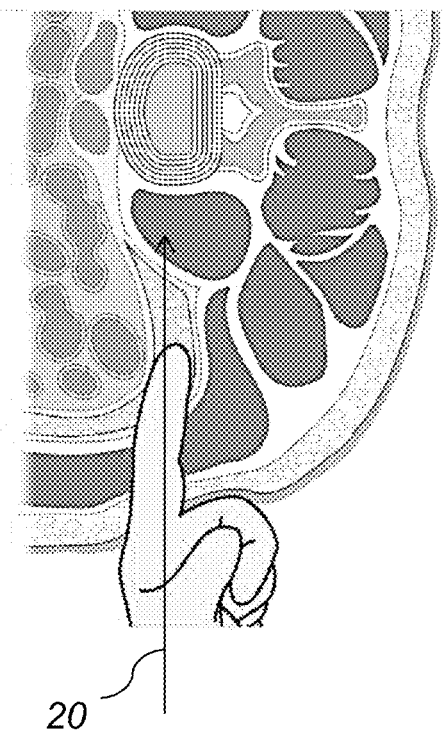
FIG. 4 depicts the entry point and direction of accessing and performing the spinal disc replacement surgery via a lateral approach, according to this invention.
Figure 5A:
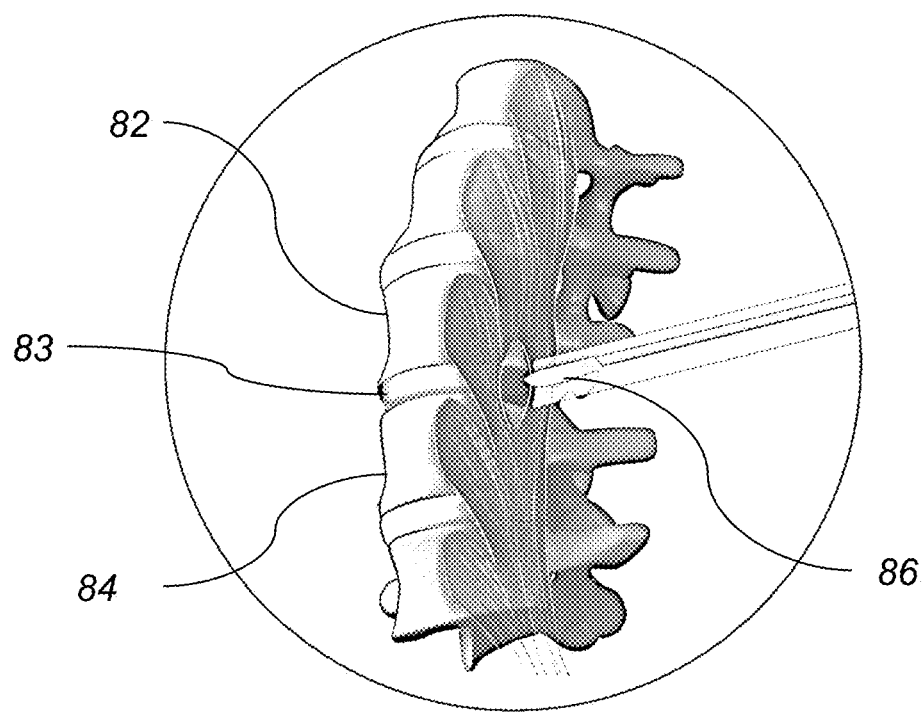
FIG. 5A to FIG. 5I are schematic diagrams of the steps for the spinal disc replacement surgery via a lateral approach, according to this invention.
Figure 5B:
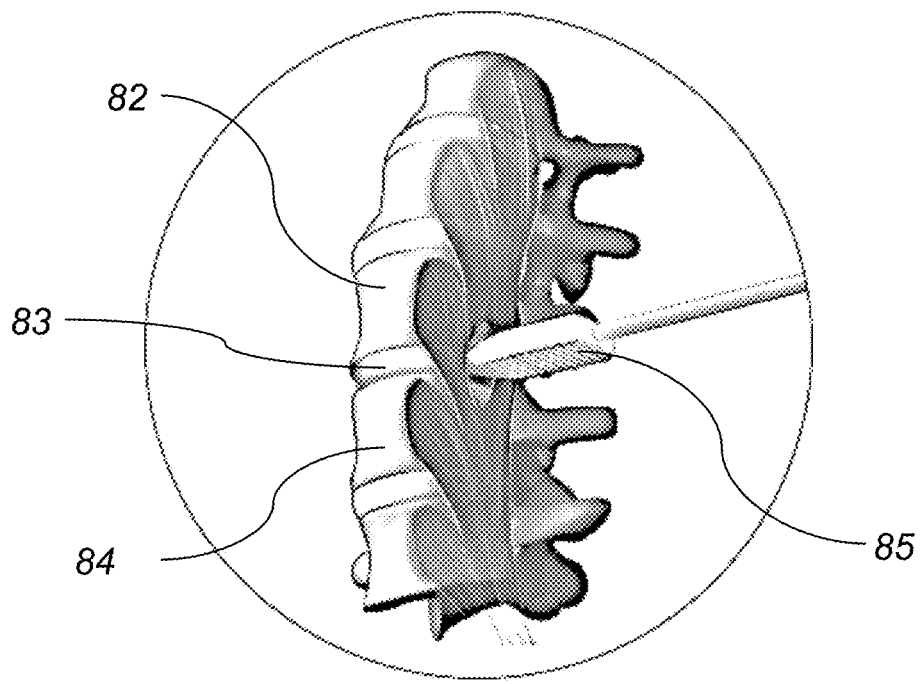
Figure 5C:
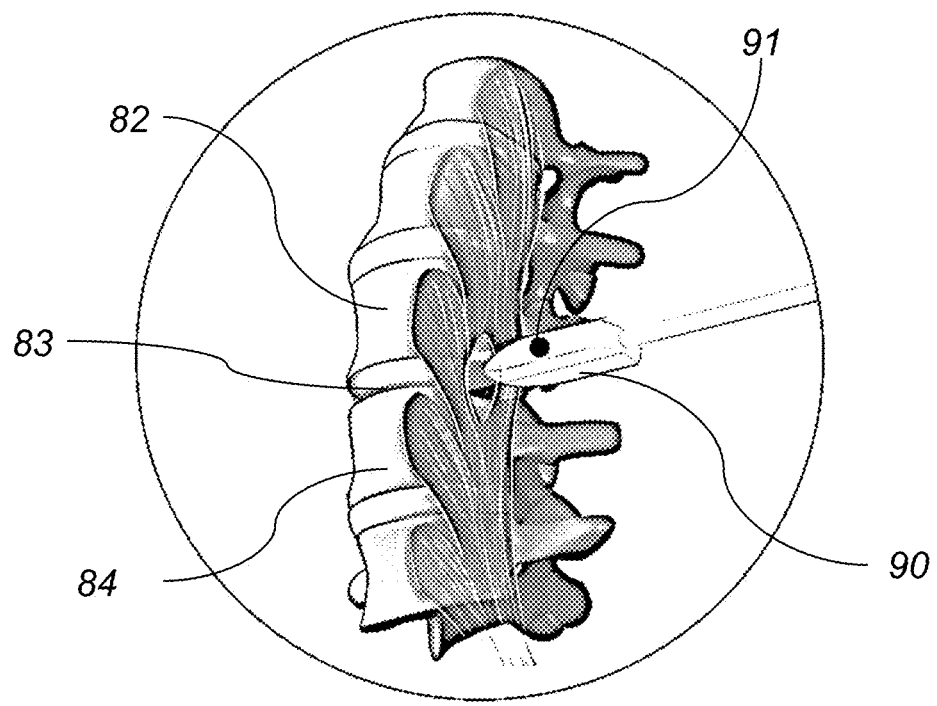
Figure 5D:
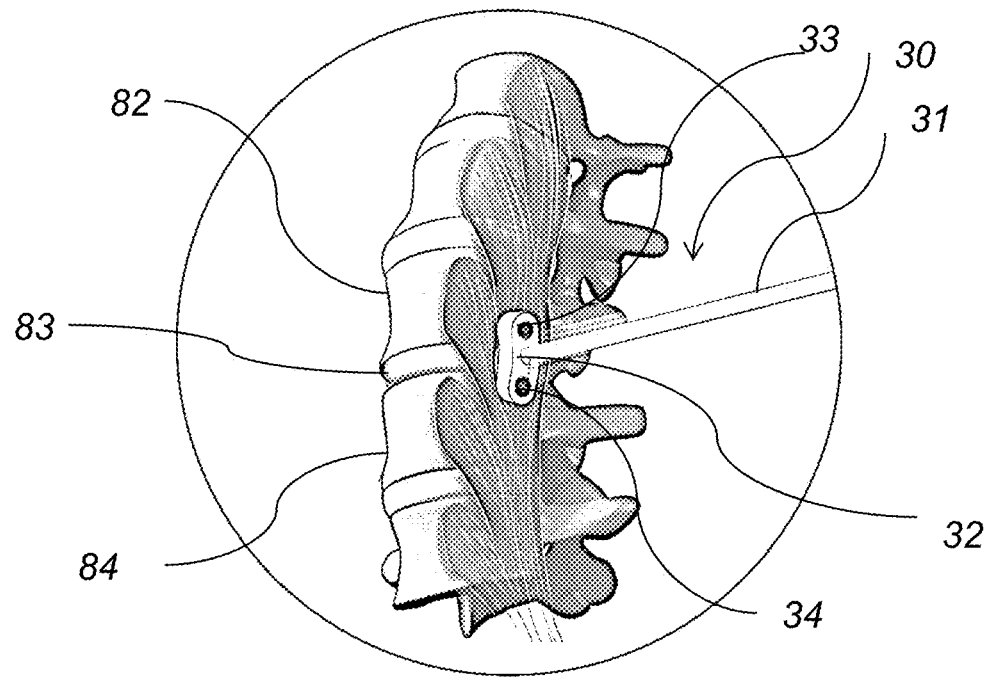
Figure 5E:
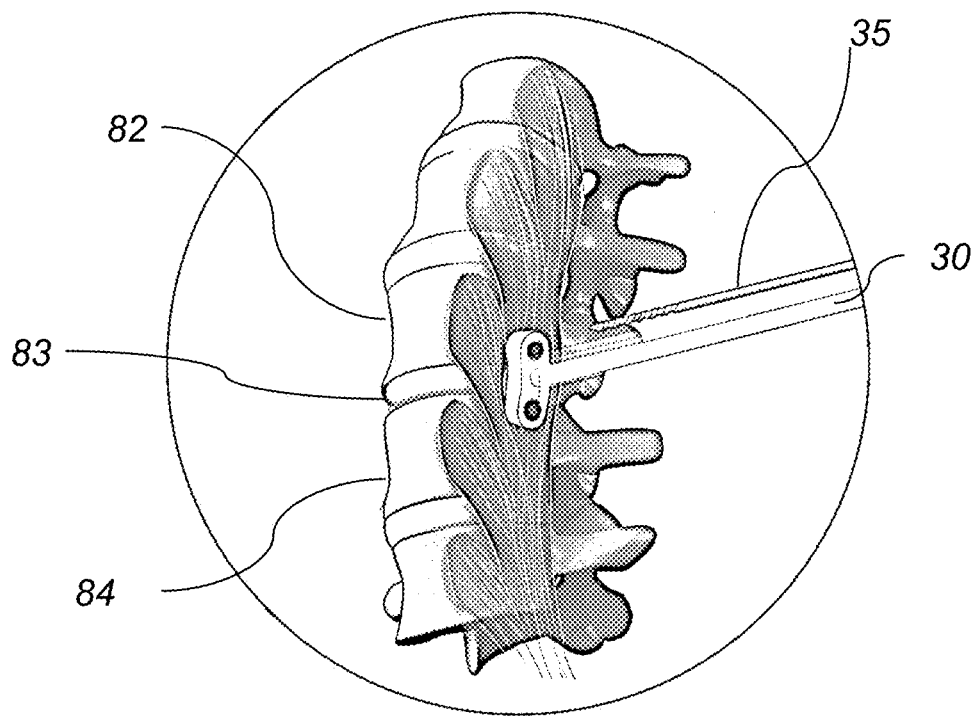
Figure 5F:
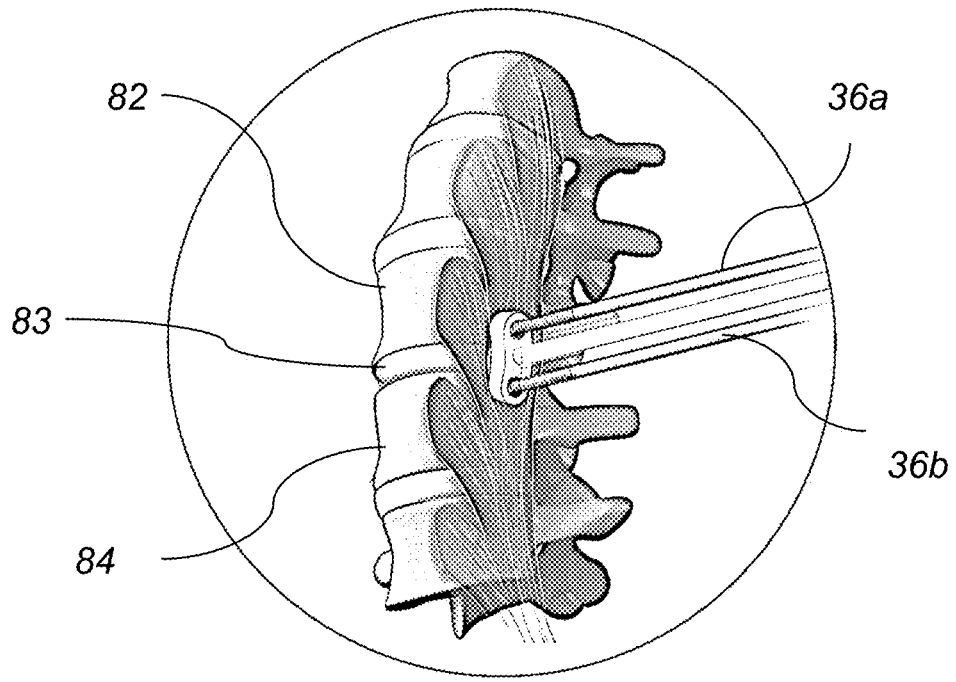
Figure 5G:
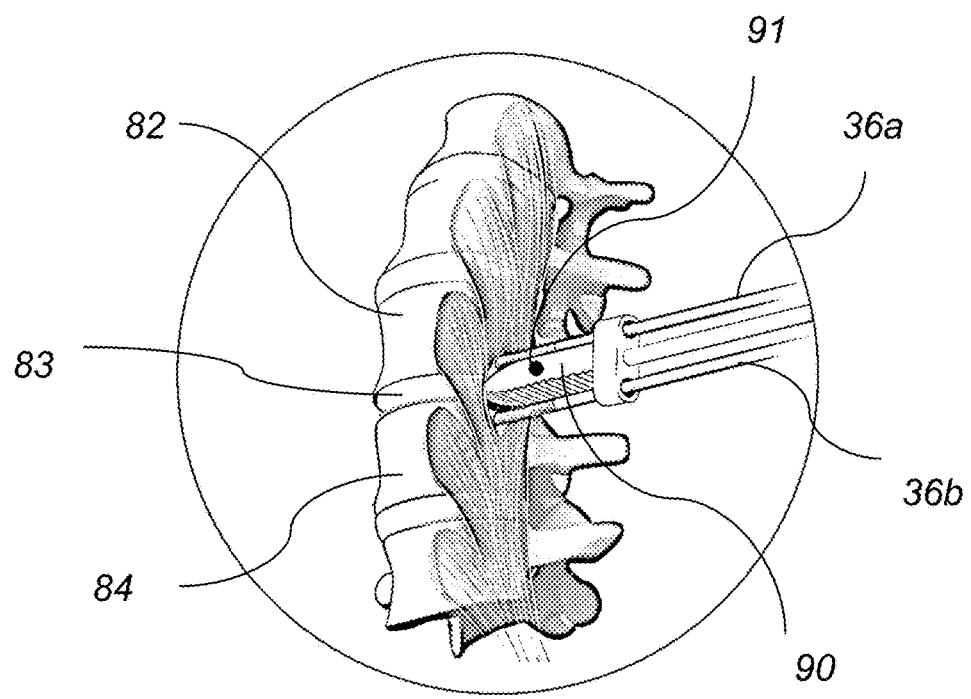
Figure 5H:
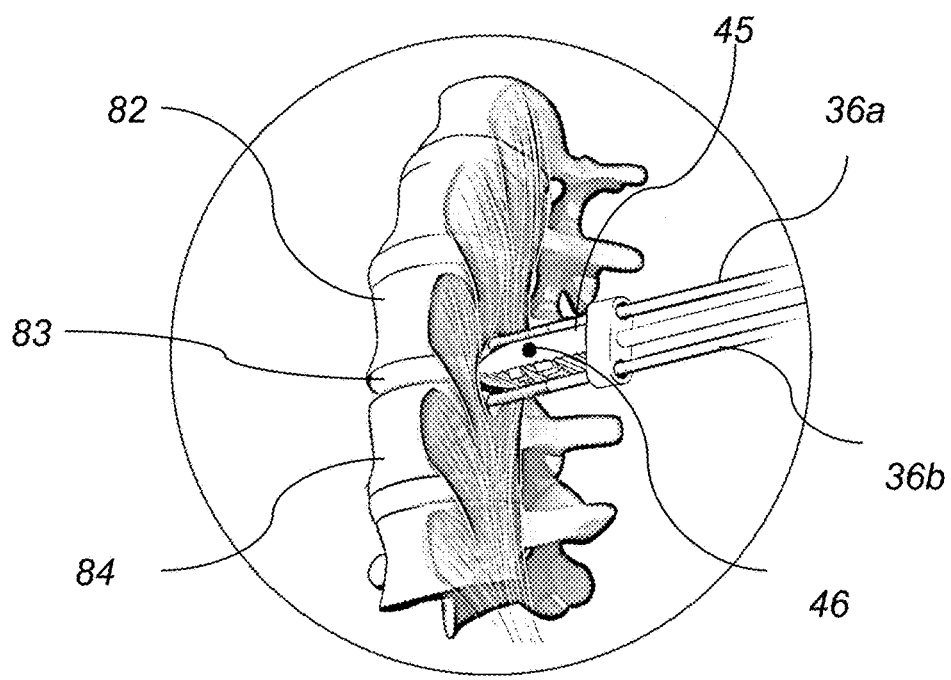
Figure 5I:
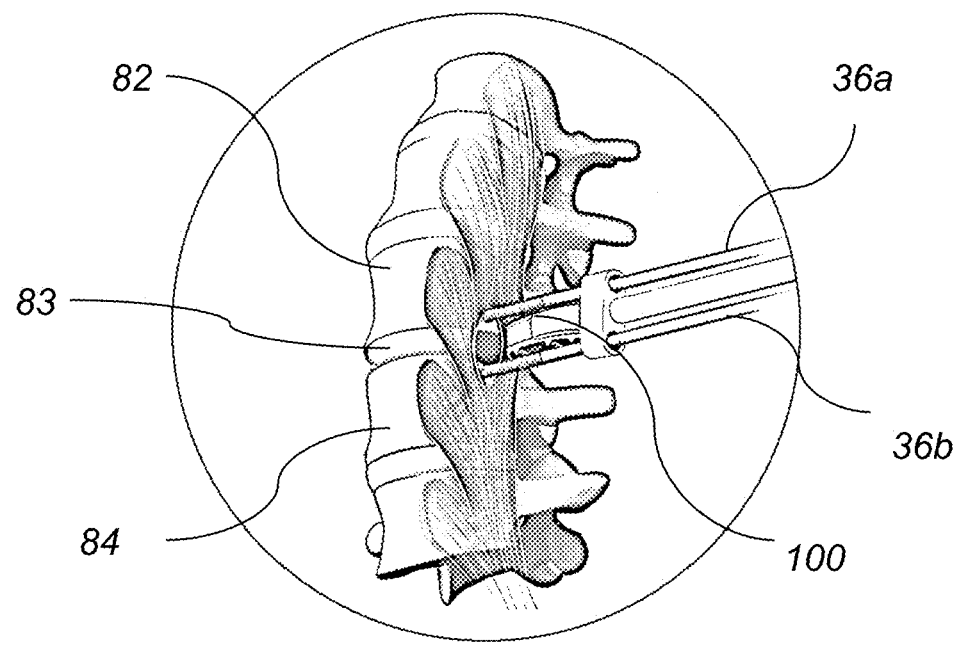

In operation, the patient is placed in the lateral decubitus position on the operation table, and anterior-posterior and lateral fluoroscopic images are taken in this lateral position, as shown in FIG. 3. A soft support between the patient and the operating table may be used to help maintain the patient's positioning. It is recommended to use a flexible operating table and to position the patient so that the iliac crest of the patient is over the table break. Slight flexion may be applied to open the patient's flank. Next, an incision is made to gain access to the surgical site along the axis 20, shown in FIG. 4. The incision is made so that the anterior third of the disc space is targeted. The abdominal oblique muscles are separated with a blunt dissection to enter the retroperitoneal space. The peritoneum is moved anteriorly with the forefinger and the blunt dissection is continued to palpate down to the psoas muscle. Next, after the correct disc space has been identified, an incision is created through the annulus fibrosis of the disc 83, and the nucleus pulposus is removed using standard surgical techniques and tools 86, as shown in FIG. 5A. Any bone spurs or osteophytes are removed, as well, and then a rasp 85 is used to prepare the superior and inferior endplates for the spinal implant, as shown in FIG. 5B. In the next step, an appropriate sized and shaped implant is determined by inserting incremental trial implants 90 into the opened disc space, as shown in FIG. 5C. In this step, trial disc implants 90 with varying footprint size, wedge angle and height are inserted in the disc space to simulate various disc configurations. The trial disc implants 90 are placed approximately 2-3 mm inside the anterior edge of the superior vertebral body, with particular concern for osteophytes. The trial depth is chosen so that in anterior-posterior (AP) views reference circles 91 on the disc implants 90 are aligned at or are dorsal to the intersection of the midpoint reference line of the respective vertebral bodies, shown in FIG. 5C. The trial implant should cover ⅔ and ¾ of the lateral endplate surface and ¾ of the AP surface. In the next steps a reference point is created that will be used in the process of cutting the teeth profile in the vertebral endplates and the insertion of the disc implant. Referring to FIG. 5D, a trial guide tool 30 is placed over the disc opening. Trial guide tool 30 includes a rod 31 and a plate 32 mounted at the distal end of the rod 31. Plate 32 has two reference openings 33, 34 that are used as guides for drilling and positioning Steinmann pins. A drill is used though the guide reference openings 33, 34 to drill openings in the adjacent superior and inferior vertebras 82, 84, respectively, shown in FIG. 5E. The depth of the drilled openings is selected based on the patient anatomy. Next, the trial guide 30 is removed and the Steinmann pins 36a, 36b are inserted in the drilled openings, as shown in FIG. 5F. In the next step, the selected trial implant 90 is mounted at the end of the trial guide 30 and is inserted in the disc space over the Steinmann pins 36a, 36b, as shown in FIG. 5G. Next, the trial implant 90 is removed and a tooth profile cutter 45 is mounted at the end of the trial guide 30 and is inserted in the disc space over the Steinmann pins 36a, 36b, and is used to cut the tooth profile that corresponds to the tooth profile of the implant in the surfaces of the upper and lower vertebras 82, 84, respectively, as shown in FIG. 5J. The tooth cutter depth is chosen so that on anterior-posterior (AP) views reference circles 46 on the tooth cutter 45 are aligned at or are dorsal to the intersection of the midpoint reference line of the respective vertebral bodies. Finally, the tooth cutter 45 is removed and the selected implant 100 is mounted at the end of the trial guide 30 and is inserted in the disc space over the Steinmann pins 36a, 36b, as shown in FIG. 5I.

Figure 8:
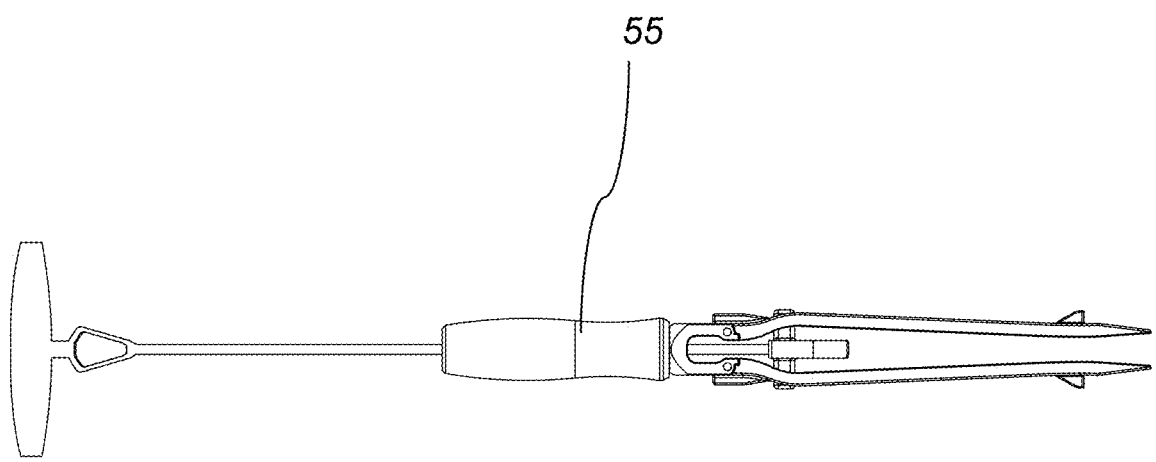
FIG. 8 depicts an inserter tool used in the spinal disc replacement surgery via a lateral approach, according to this invention.

In some embodiments, an inserter 55 is passed over the Steinmann pins 36a, 36b, to ensure correct placement of the implant, as shown in FIG. 6A. The Steinmann pin nuts are then inserted over the inserter 55 using the Steinmann pin nut inserter to secure the construct and ensure accurate placement. Locking to the inserter 55 also helps distract the disc space when the implant is inserted. In this case, the implant 100 is connected to the advancing section 57 of an inserter 55 and the implant depth setting is adjusted to position the implant in the desired lateral position within the disc space, as shown in FIG. 6B. Once the implant is positioned in the proper location, the blades 56a, 56b of the inserter 55 self deploy and leave behind the implant 100 in place. In one example inserter 55 is a liquid inserter manufactured by In'Tech Medical S.A.S., France, shown in FIG. 8. If necessary, implant 100 may be removed from the disc space by connecting the tip of a removal tool 50 to the recesses 118, 138 of the implant 100 and then impacting a slap hammer that attaches to the removal tool 50 until the implant is freed, as shown in FIG. 6C.

Figure 7A:
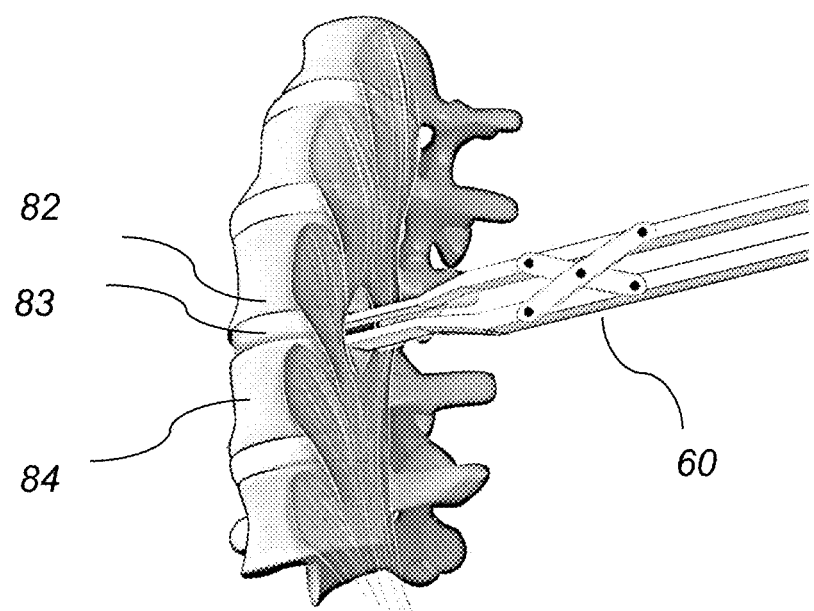
FIG. 7A to FIG. 7G are schematic diagrams of the steps of another embodiment of the spinal disc replacement surgery via a lateral approach, according to this invention.
Figure 7B:
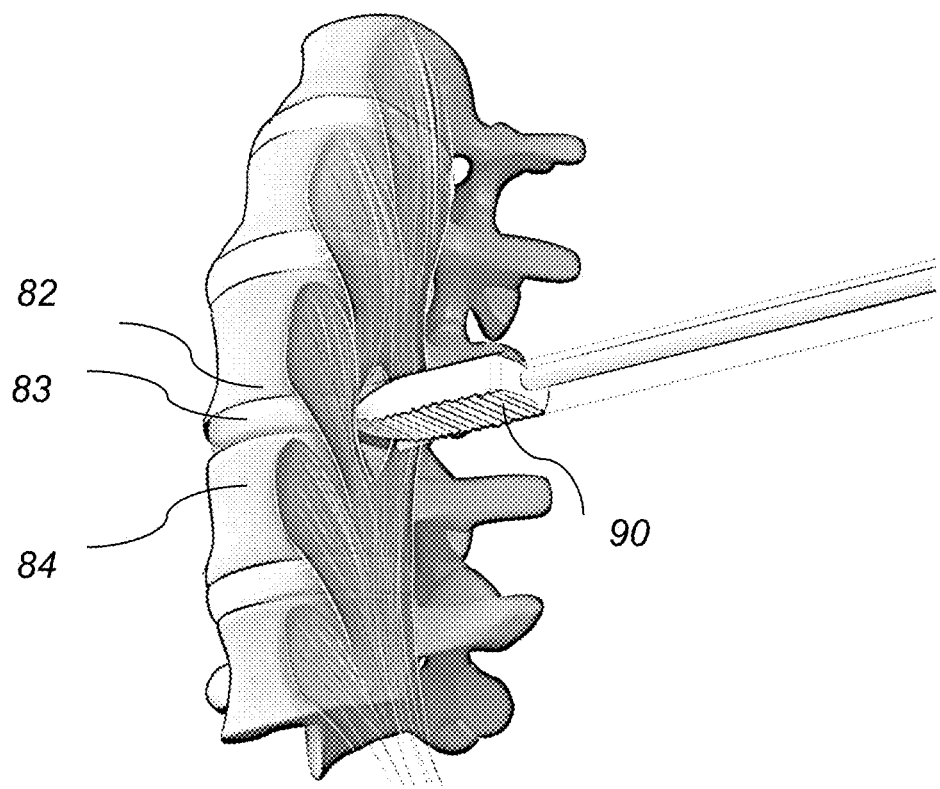
Figure 7C:
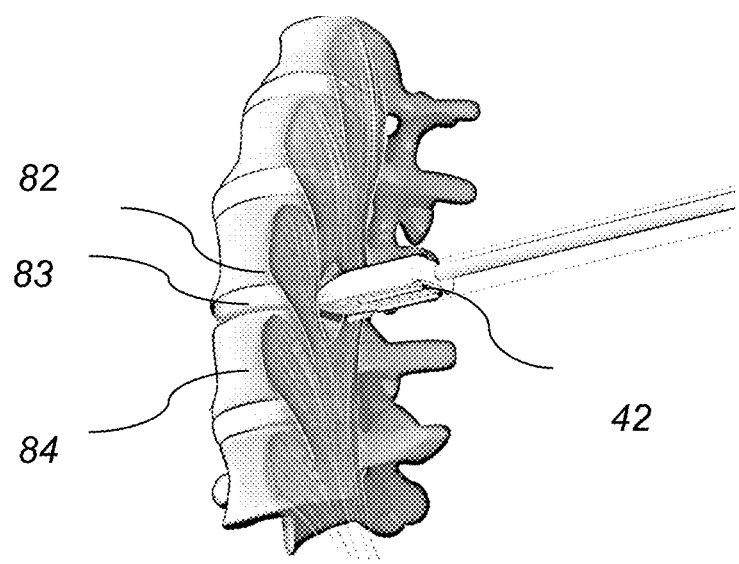
Figure 7D:
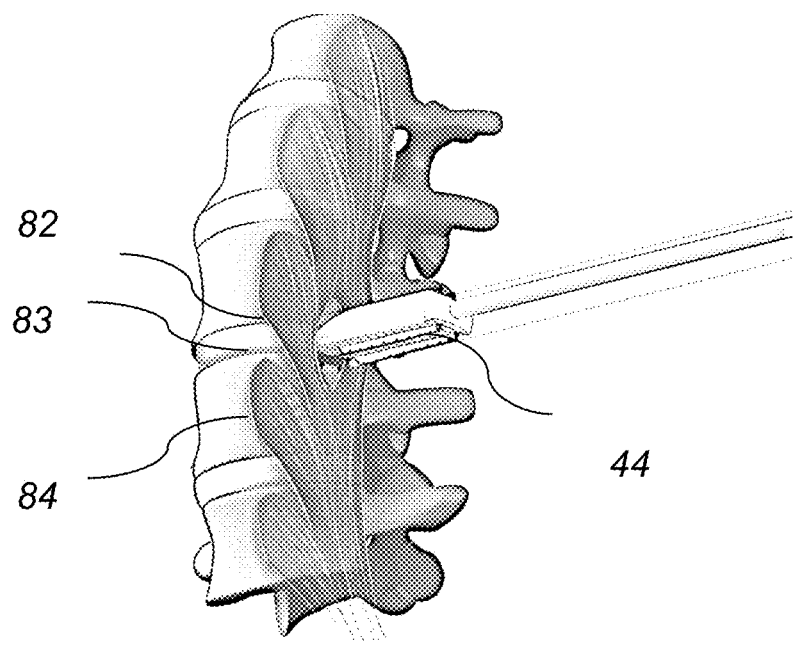
Figure 7E:
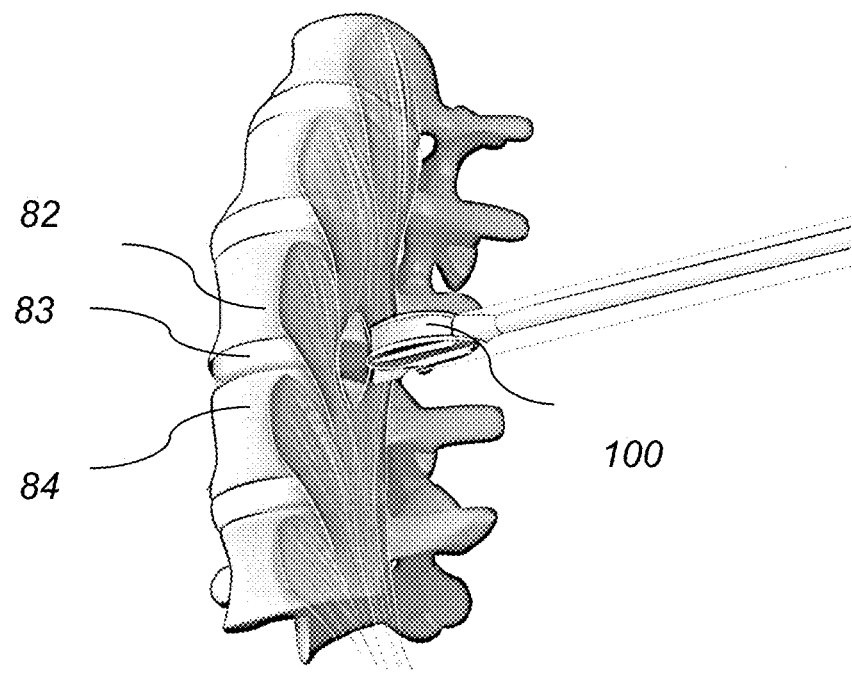
Figure 7F:
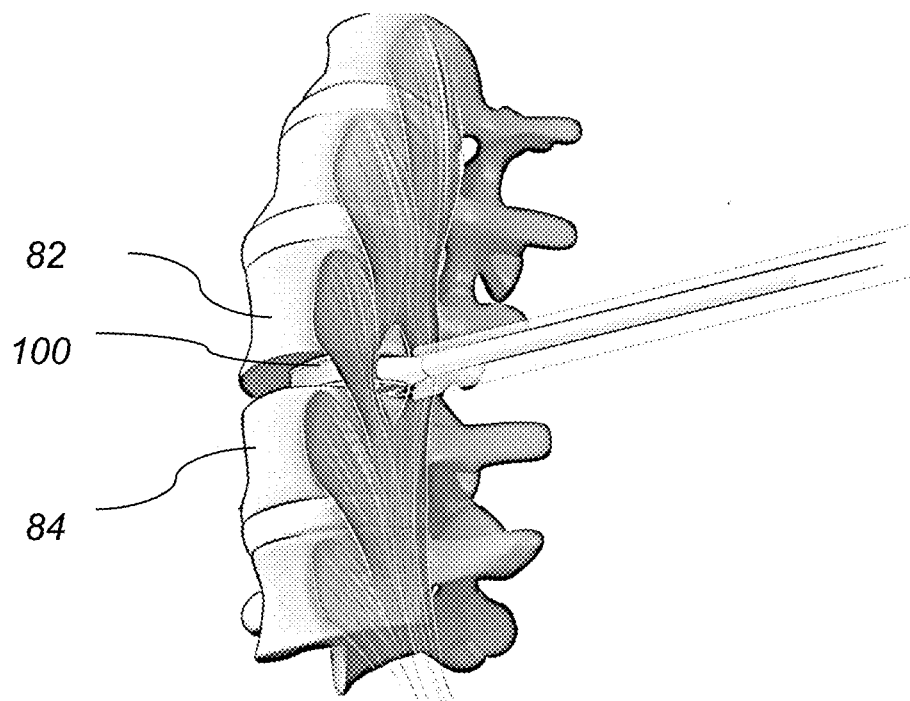
Figure 7G:
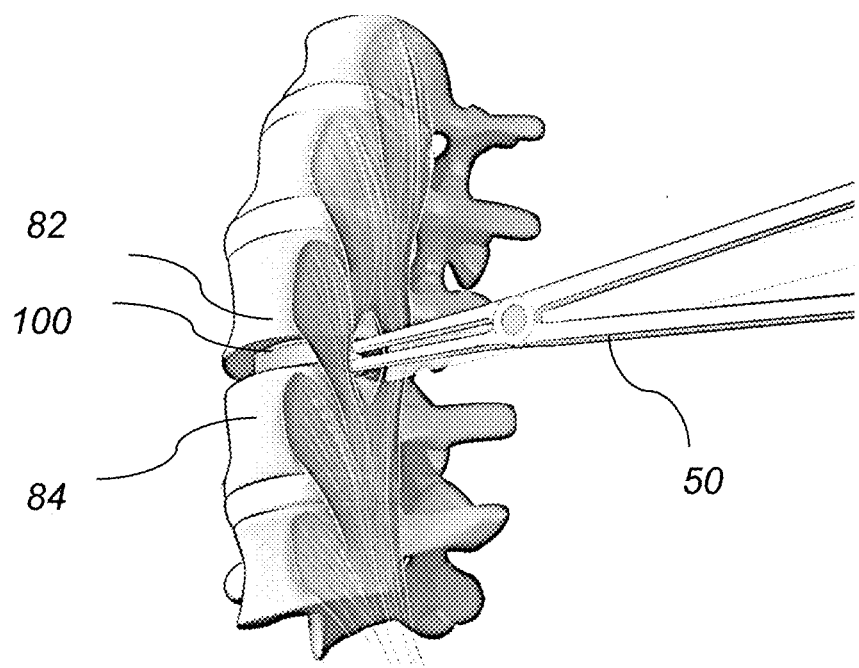

Referring to FIG. 7A-7H, in another embodiment, after the correct disc space has been identified, an incision is created through the annulus fibrosis of the disc 83 and the nucleus pulposus is removed using standard surgical techniques. Any bone spurs or osteophytes are removed, as well, and then a rasp 85 is used to prepare the superior and inferior endplates for the spinal implant, as was shown in FIG. 5B. In the next step, a parallel distractor tool 60 is used to distract the disc space equally bi-laterally over an approximately 5 minute period, as shown in FIG. 7A. The purpose of this disc space stretching is to stretch the surrounding ligaments and to restore the disc space to its natural height. In cases where sufficient distraction cannot be achieved, the disc is excised to the posterior longitudinal ligament and, if necessary, the annulus is released both inferiorly and superiorly to allow the disc height to be re-established. In the next step, an appropriate sized and shaped implant 90 is determined by inserting incremental trial implants 90 into the opened disc space, as shown in FIG. 7B. In this step, trial disc implants 90 with varying footprint size, wedge angle and height are inserted in the disc space to simulate various disc configurations. The trial disc implants 90 are placed approximately 2-3 mm inside the anterior edge of the superior vertebral body, with particular concern for osteophytes. The trial depth is chosen so that in anterior-posterior (AP) views reference circles 91 on the disc implants 90 are aligned at or are dorsal to the intersection of the midpoint reference line of the respective vertebral bodies. The trial implant should cover ⅔ and ¾ of the lateral endplate surface and ¾ of the AP surface. In the next step, a half rail cutter 42 that corresponds to the selected trial disc implant 90 is advanced into the disc space, as shown in FIG. 7C. The half rail cutter 42 is centered and is oriented at an appropriate angle that bisects the angles of the superior and inferior vertebrae. The purpose of the rail cutter is to reduce the insertion force and to avoid retrolisthesis while inserting the implant into the intra-discal space. Next, a full rail cutter 44 that corresponds to the half rail cutter 42 is advanced into the disc space, as shown in FIG. 7D. The half rail tracks guide the insertion of the full rail cutter 44. The rail cut depths are graduated in 0.5 mm increments between the half cutter 42, the full cutter 44 and the final implant 100. After insertion of the full rail cutter 44, a lateral X-ray is taken and saved on the monitor to verify visually the appropriate depth and act as a reference for the seating of the implant. The rail cutters 42, 44 may be used multiple times after cleaning out bone to provide better cutting ability. Next, the disc inserter tip that corresponds to the implant height is lightly threaded on to the implant inserter shaft and the selected implant 100 is attached to the tip and the shaft is rotated to hold the implant firmly, as shown in FIG. 7E. Since both implant sides are identical, the implant 100 may be inserted with either side up. Next, a tamp is threaded onto the multi-shaft and then mated to the anterior edge of the implant. A mallet is used to gently strike the handle of the multi-shaft and thereby to slowly push the implant further into the disc space, as shown in FIG. 7F. The implant is advanced into the disc space until it reaches the same position as the saved X-ray with the full rail cutter. If necessary, implant 100 may be removed from the disc space by connecting the tip of a removal tool 50 to the handles of the implant 100 and then impacting a slap hammer that attaches to the removal tool until the implant is freed, as shown in FIG. 7G.

Figure 9A:
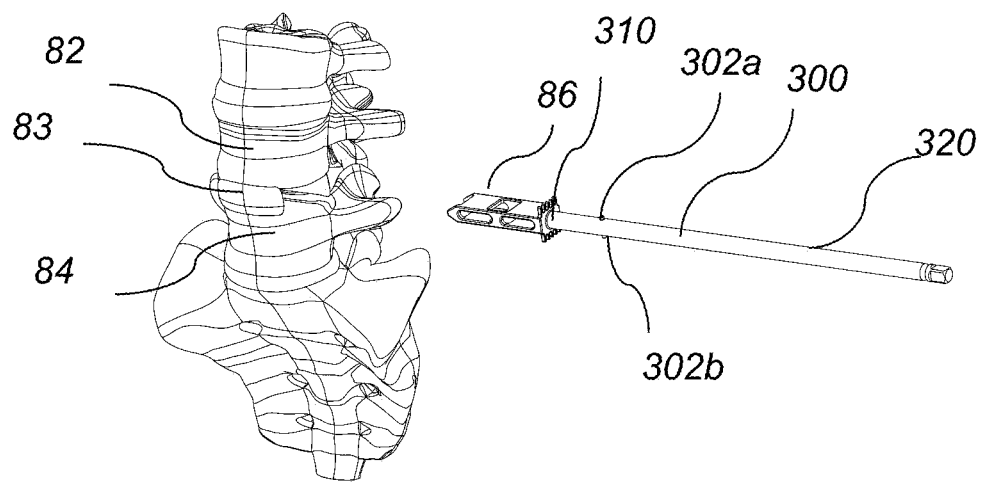
FIG. 9A to FIG. 9P are schematic diagrams of the steps of another embodiment of the spinal disc replacement surgery via a lateral approach, according to this invention.
Figure 9B:
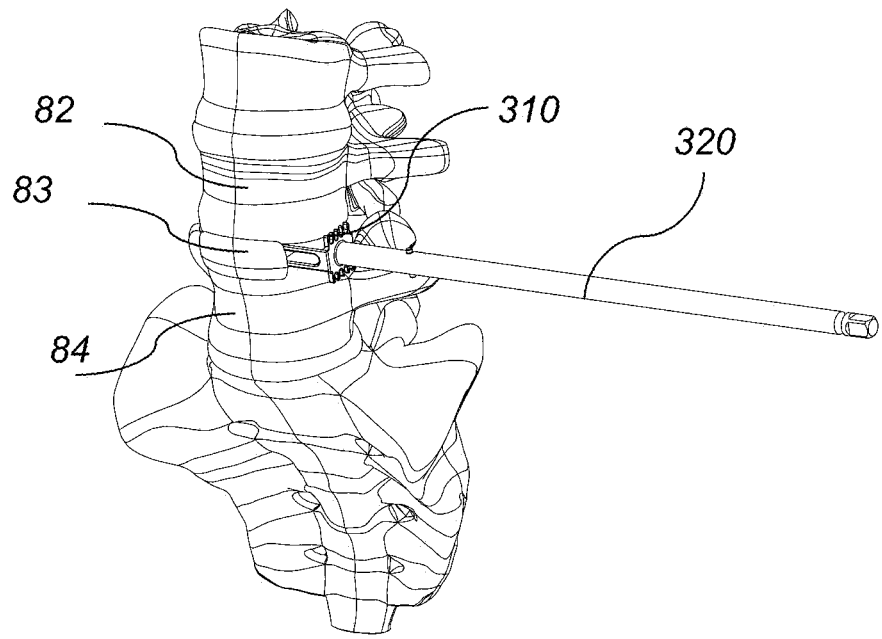
Figure 9C:
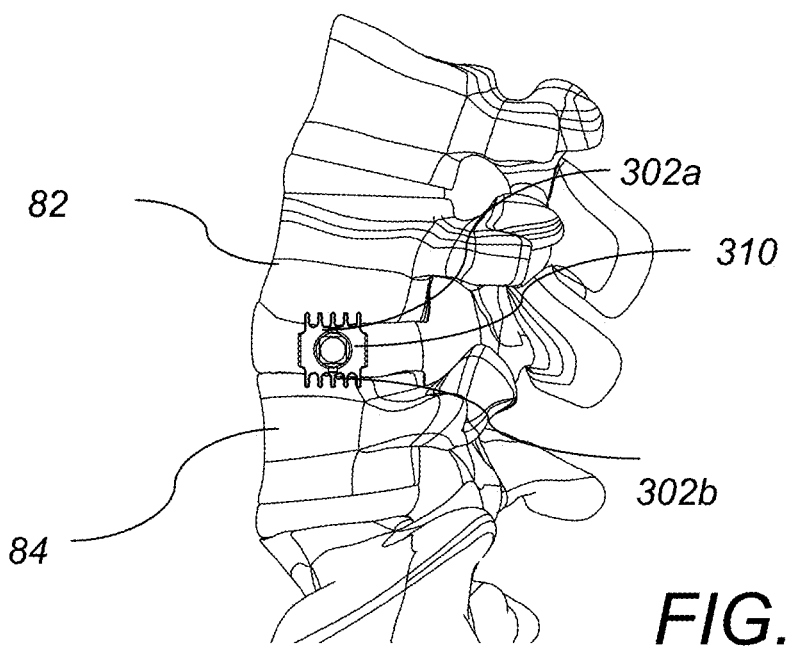
Figure 9D:
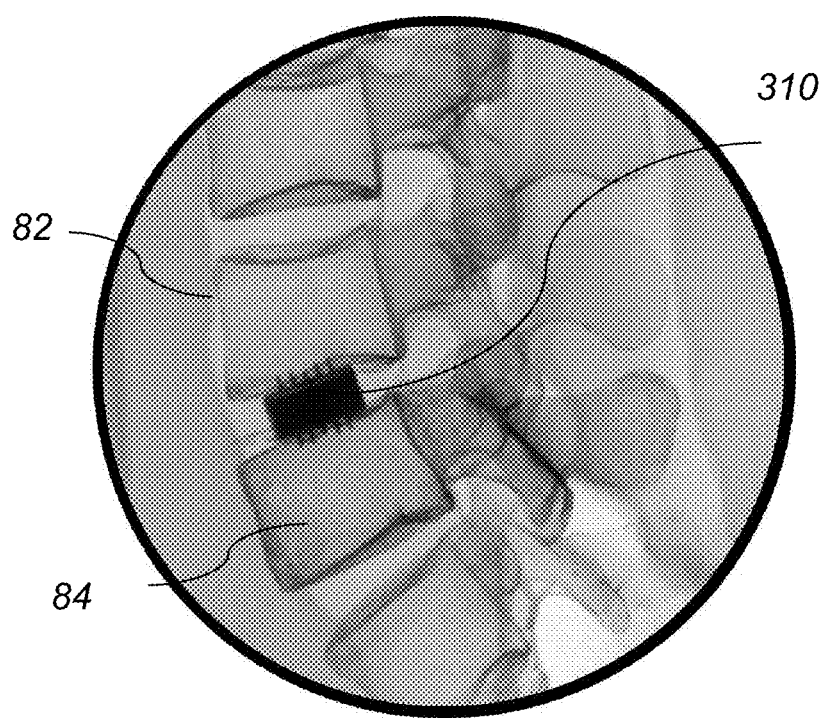
Figure 9E:
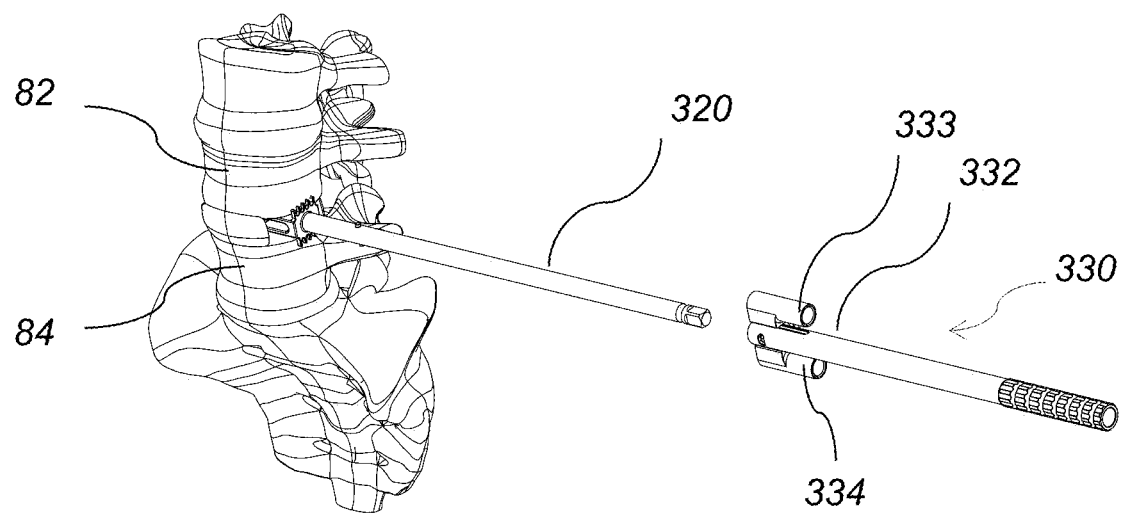
Figure 9F:
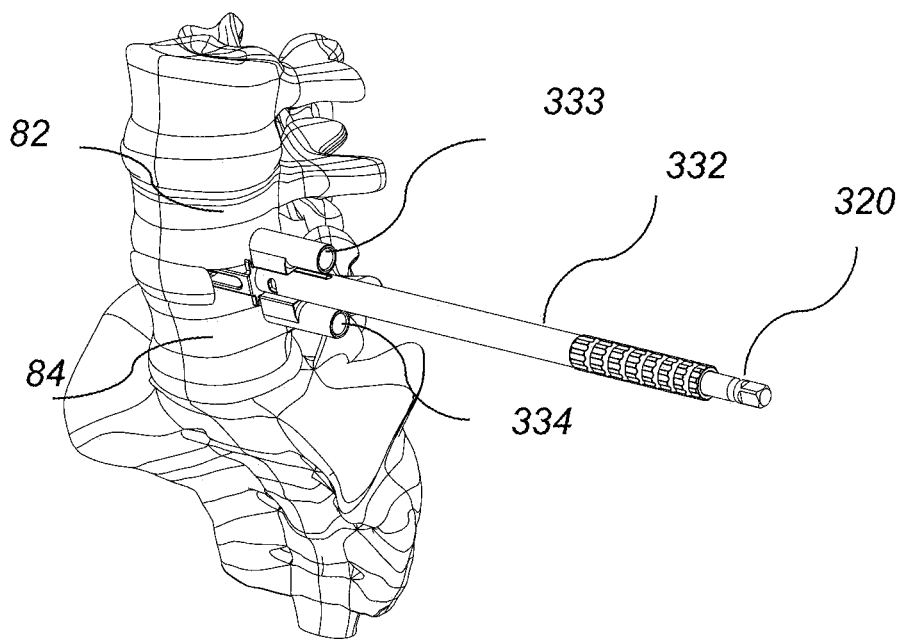
Figure 9G:
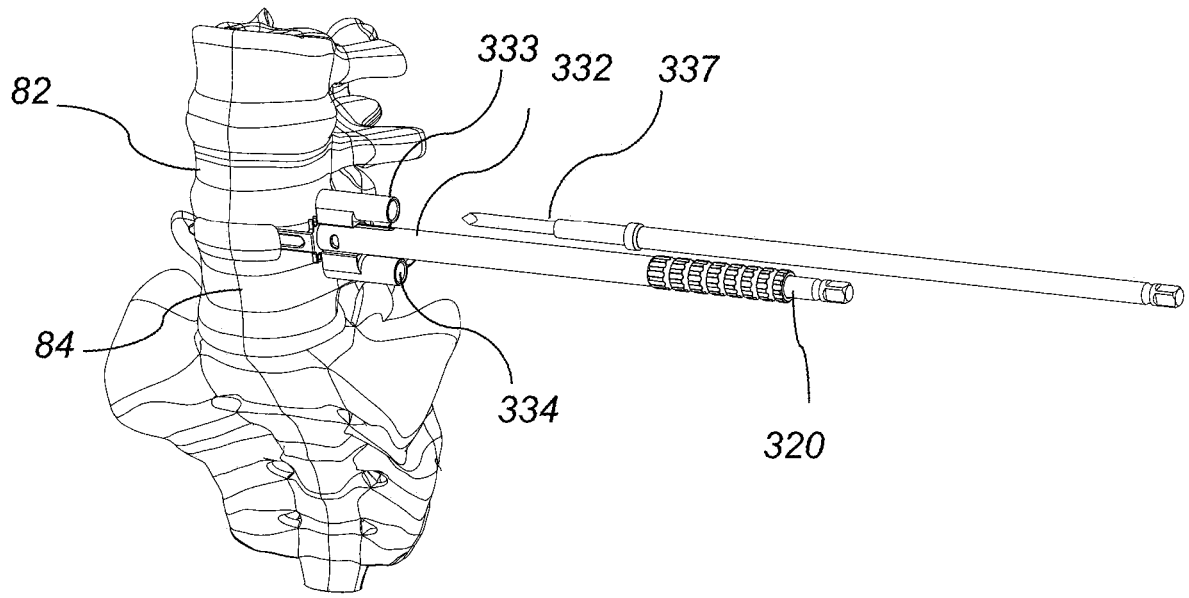
Figure 9H:
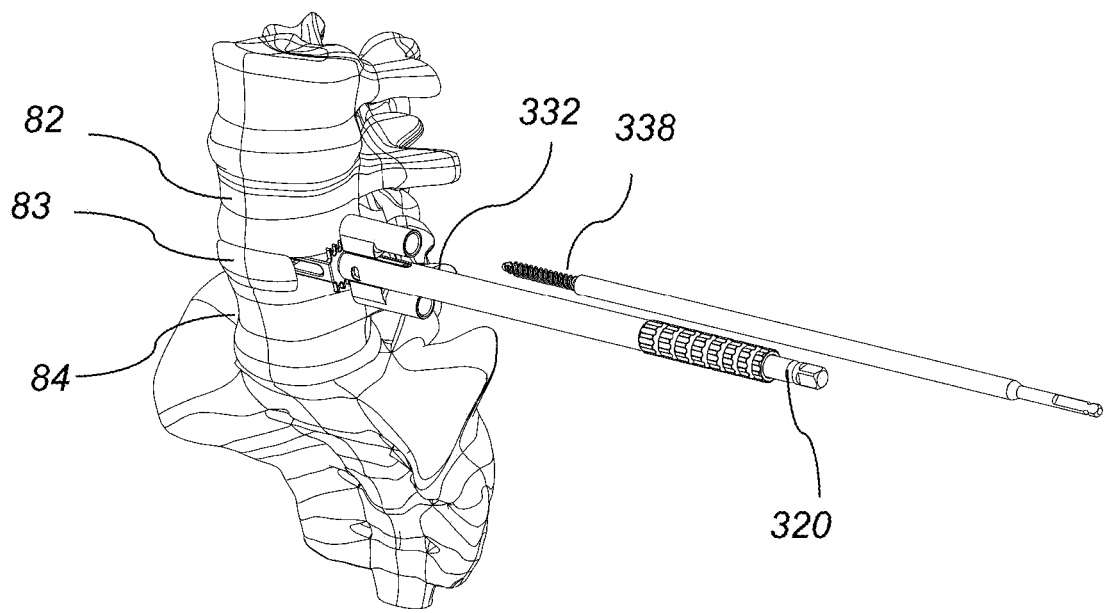
Figure 9I:
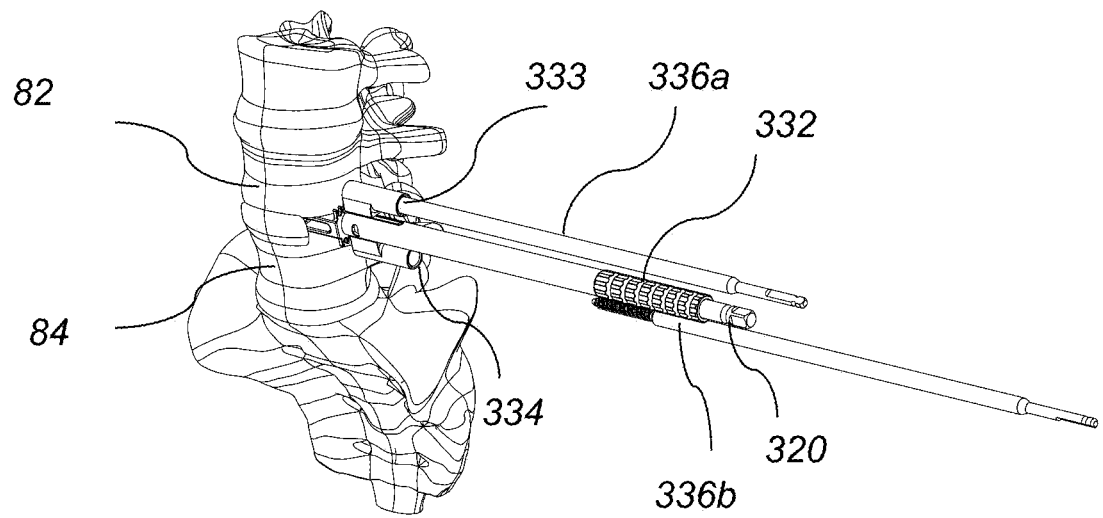
Figure 9J:
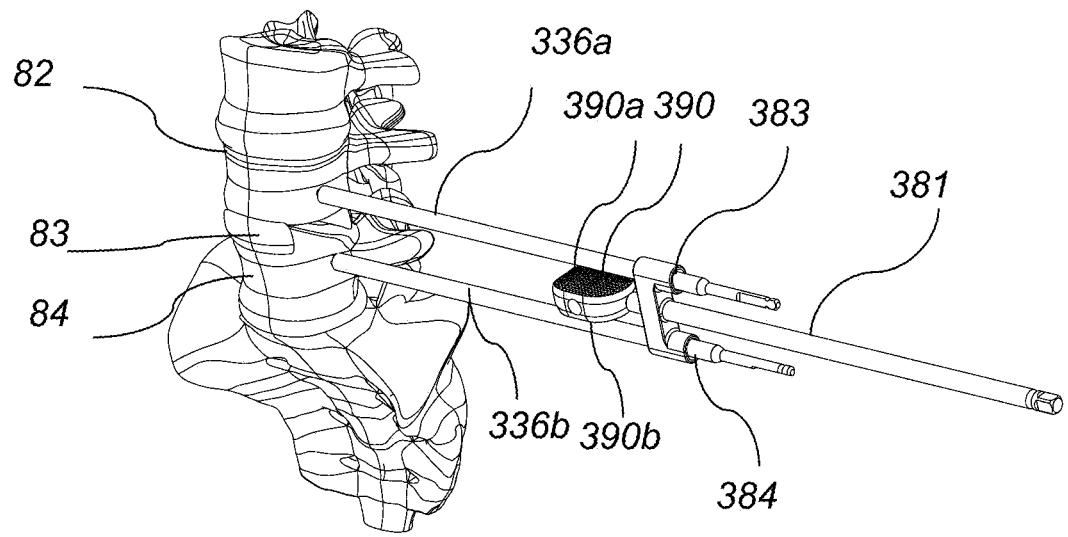
Figure 9K:
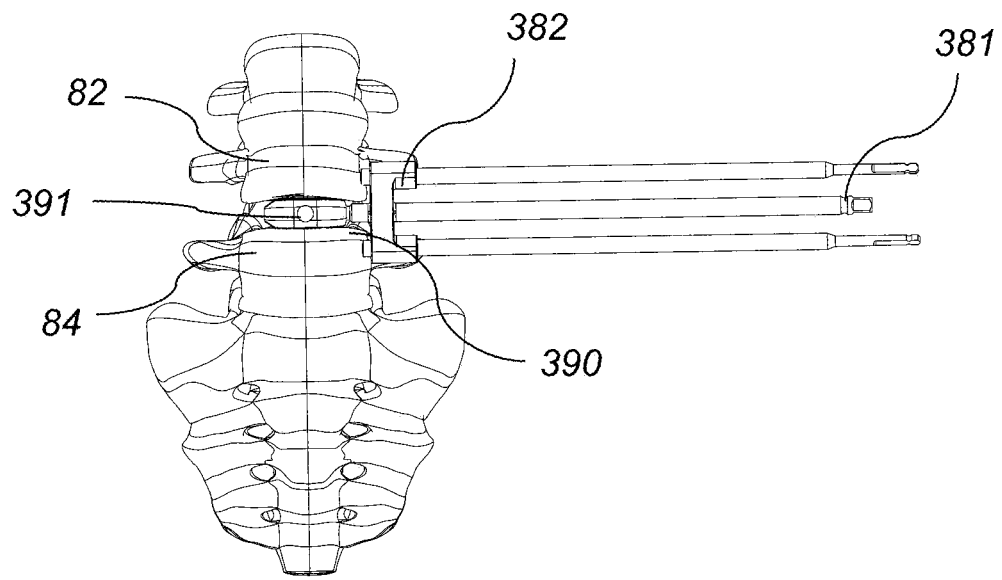
Figure 9L:
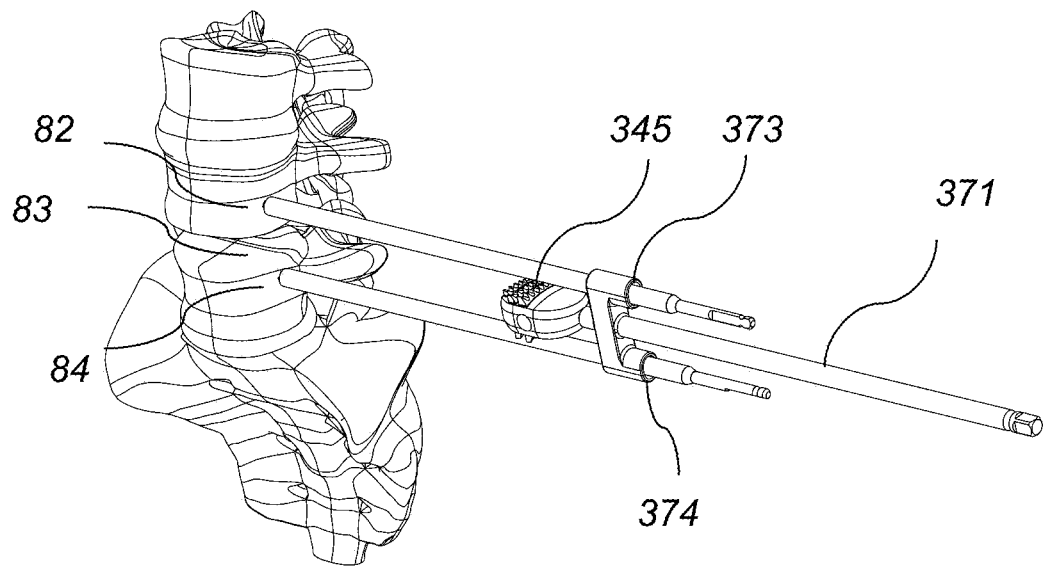
Figure 9M:
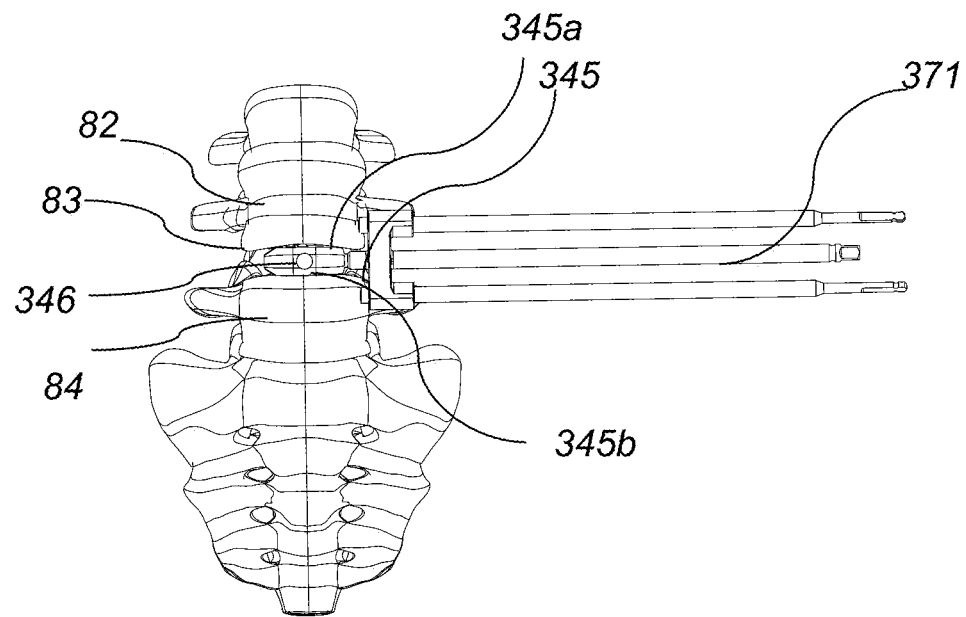
Figure 9N:
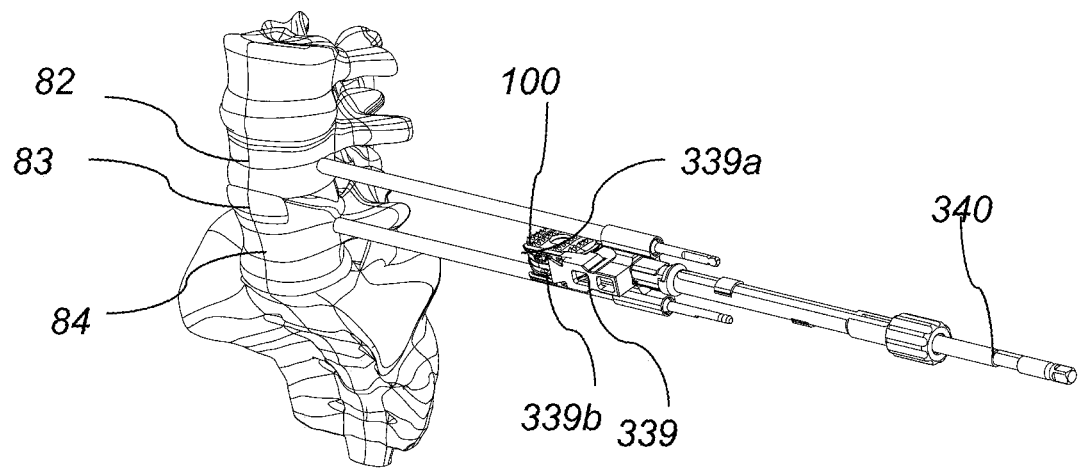
Figure 9O:
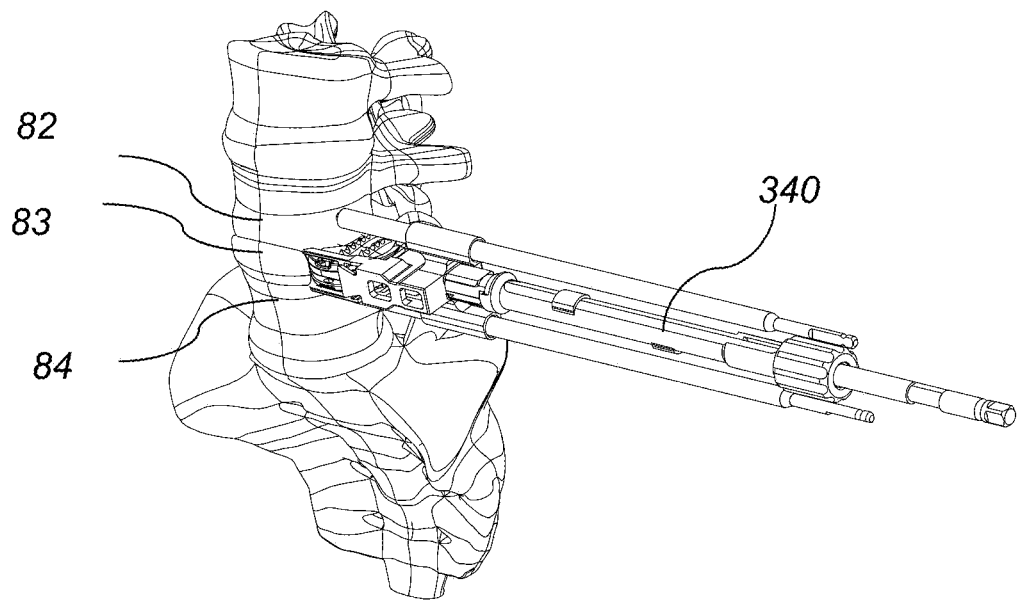
Figure 9P:
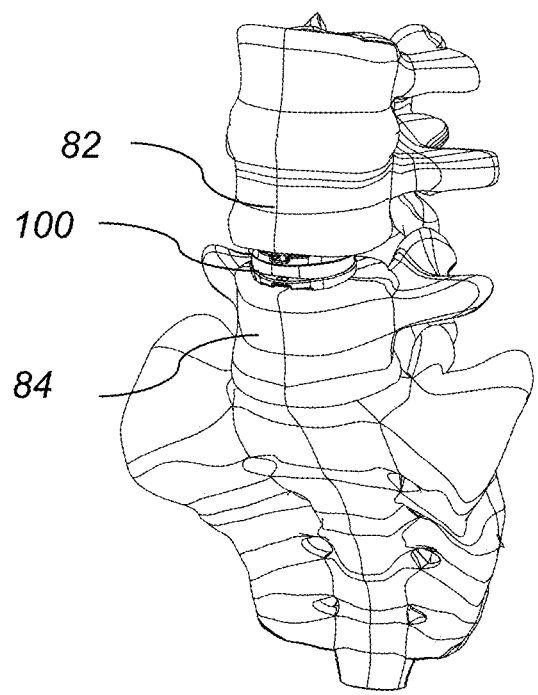

Referring to FIG. 9A-9Q, in another embodiment, after the correct disc space has been identified, an incision is created through the annulus fibrosis of the disc 83 and the nucleus pulposus is removed using standard surgical techniques. Next, a centering broach tool 300 is inserted in the space between the superior vertebra 82 and inferior vertebra 84 until a stop endplate 310 of the centering broach tool 300 stops against the sides of the vertebral bodies 82, 84, as shown in FIG. 9A and FIG. 9B. Centering broach tool 300 includes an elongated shaft 320 and a broach 86, which is attached at the distal end of the elongated shaft 320. The proximal end of the broach 86 includes the stop endplate 310, as shown in FIG. 9A and will be described below. Alignment pins 302a, 302b on the elongated shaft 320 are used to establish the lateral center. The position of the centering broach 86 is confirmed under fluoroscopic imaging, as shown in FIG. 9D. Next, a lateral center position is selected on the Steinmann pin drill guide 330, based on the fluoroscopic image reading, and the drill guide 330 is slid over the broach tool shaft 320 until it stops on the desired position and the drill openings 333, 334 line up with laser markings, as shown in FIG. 9E and FIG. 9F. The position of the drill guide 330 is confirmed under fluoroscopic imaging. Next, an awl 337 is inserted into the Steinmann pin drill guide openings 333, 334 and is impacted until a desired depth in each of the vertebrae 82, 84 is reach, as shown in FIG. 9G. The depth of the impacted awl 337 is confirmed under fluoroscopic imaging. Next, a tap 338 is inserted into the Steinmann pin drill guide openings 333, 334 and is advanced until the desired depth in each of the vertebrae 82, 84 is reach, as shown in FIG. 9H. The depth of the advanced tap is confirmed under fluoroscopic imaging. Next, the Steinmann pins 336a, 336b are inserted into the Steinmann pin drill guide openings 333, 334 and are advanced until the desired depth in each of the vertebrae 82, 84 is reach, as shown in FIG. 9I. The depth of the advanced tap 338 is confirmed under fluoroscopic imaging. In the next step, the selected trial implant 390 is mounted at the end of the trial guide rod 381 and is inserted in the disc space over the Steinmann pins 336a, 336b, as shown in FIG. 9J. Barrels 390a, 390b are positioned on top and bottom of the trial implant 390 at an offset height, respectively. Barrels 390a, 390b help distract the disc space 83 and the position of the Steinmann pins drives the distraction. The trial implant 390 is impacted into the disc space 83 until the desired depth is achieved. The position of the trial implant 390 in the disc space 83 is confirmed under fluoroscopic imaging. An opening 391 in the sidewall of the trial implant 390 corresponds to the center of the implant 100. Next, the trial implant 390 is removed and a tooth profile cutter 345 is mounted at the end of the cutter inserter rod 371 and is inserted in the disc space over the Steinmann pins 336a, 336b, and is used to cut the tooth profile that corresponds to the tooth profile of the implant in the surfaces of the upper and lower vertebras 82, 84, respectively, as shown in FIG. 9L. Barrels 345a, 3350b are positioned on top and bottom of the tooth profile cutter 345 at an offset height so that they don't interfere with the tooth profile cutter teeth, respectively. The barrels 345a, 345b on the tooth profile cutter 345 help distract the disc space 83 and the position of the Steinmann pins drives the distraction. The tooth profile cutter 345 is impacted into the disc space 83 until the desired depth is achieved, as shown in FIG. 9M. The position of the tooth profile cutter 345 in the disc space 83 is confirmed under fluoroscopic imaging. An opening 346 in the sidewall of the tooth profile cutter 345 corresponds to the center of the implant 100. Finally, the tooth cutter 345 is removed and the selected implant 100 is mounted at the end of the implant inserter rod 340 and is inserted in the disc space 83 over the Steinmann pins 336a, 336b, as shown in FIG. 9N. Barrels 339a, 339b are positioned on top and bottom of the implant 100 at an offset height so that they don't interfere with the implant teeth, respectively. The barrels 339a, 339b on the implant guide end 339 help distract the disc space 83 and the position of the Steinmann pins drives the distraction. The position of the implant 100 is confirmed under fluoroscopic imaging. Finally, the implant inserter tool 340 is disengaged from the implant 100 and removed, the Steinmann pins are removed, the pin holes in the vertebrae 82, 84 are filled with biocompatible material and the suture is closed, leaving behind the implant 100 in the disc space 83, as shown in FIGS. 9O and 9P.

Figure 10A:
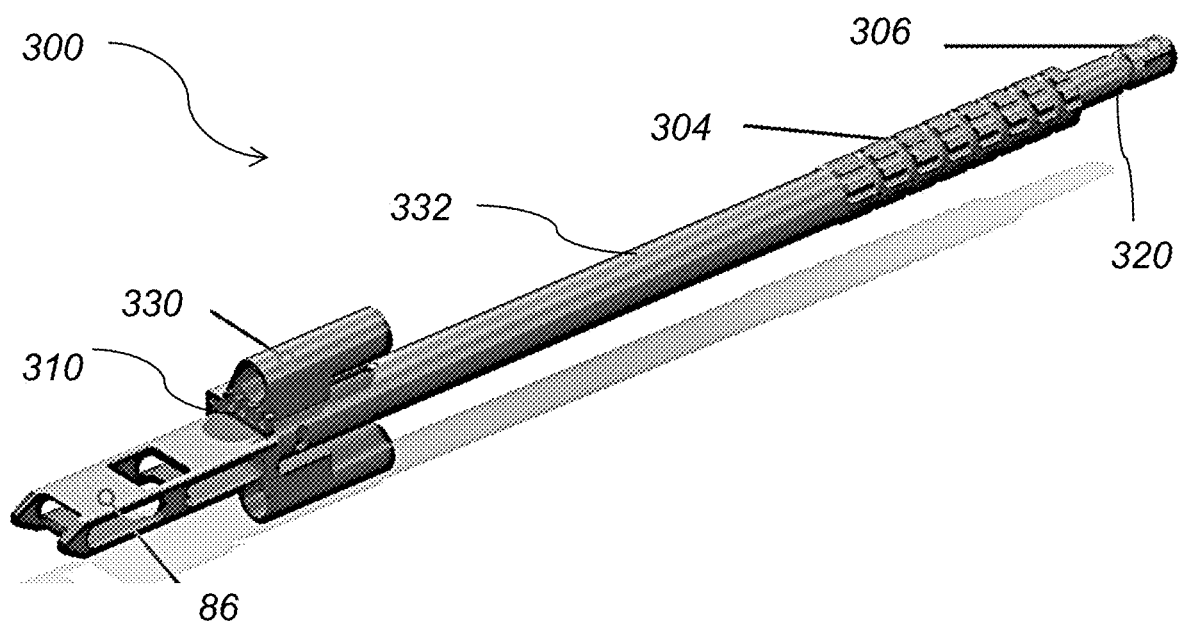
FIG. 10A to FIG. 10F depict a centering broach tool used in the spinal disc replacement surgery via a lateral approach, according to this invention.
Figure 10B:
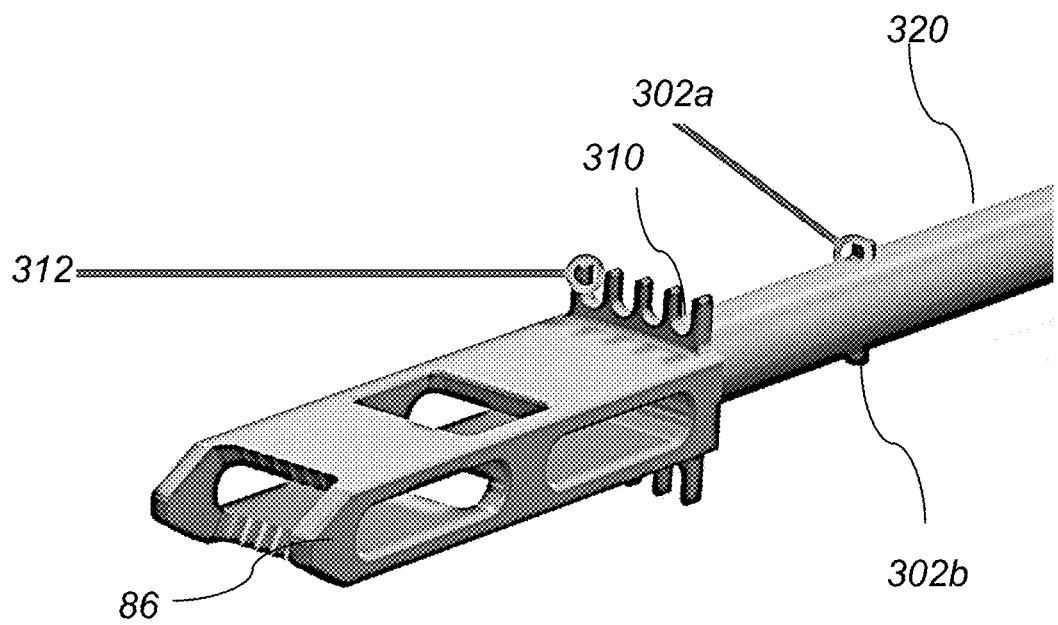
Figure 10C:
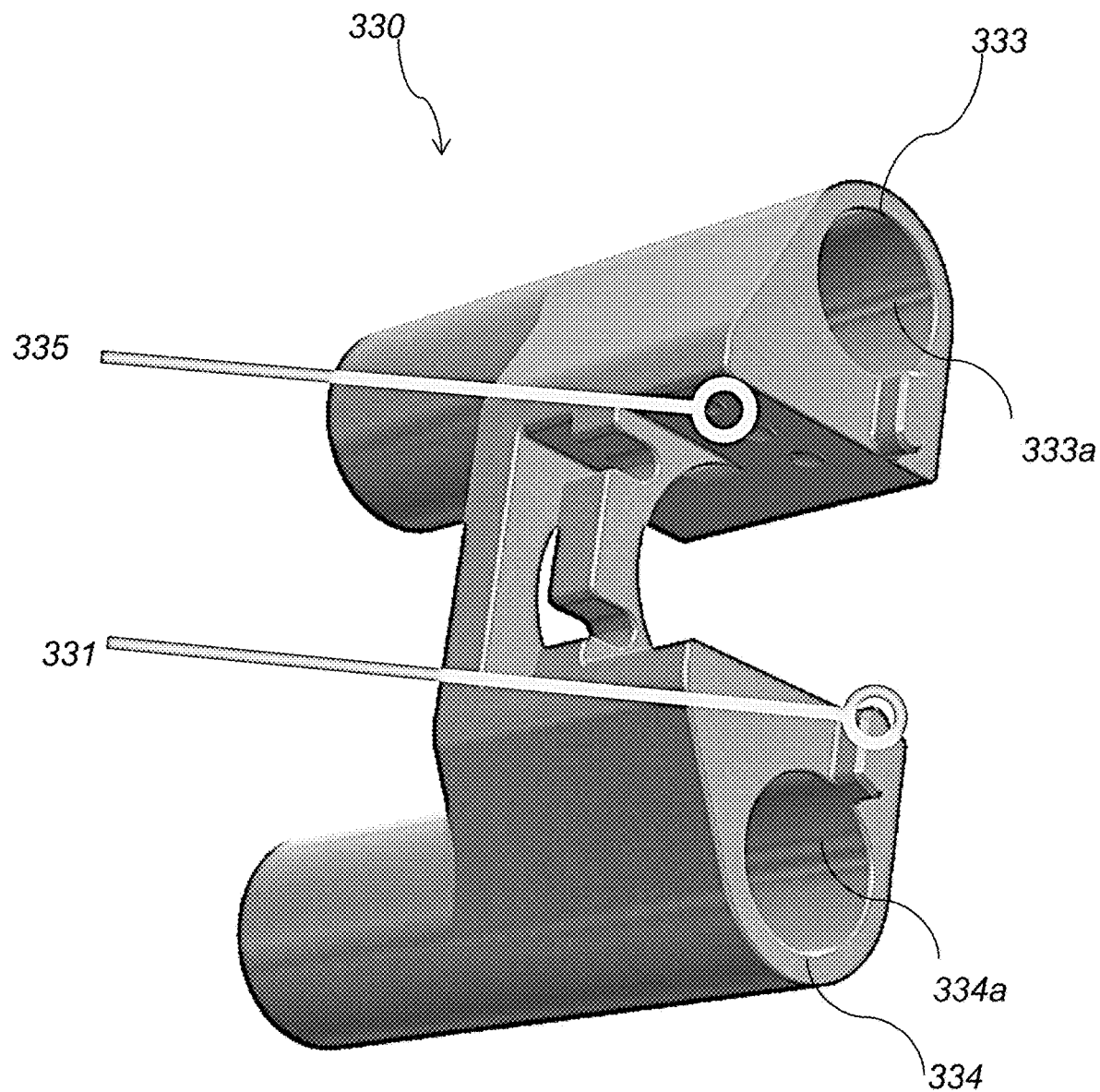
Figure 10D:
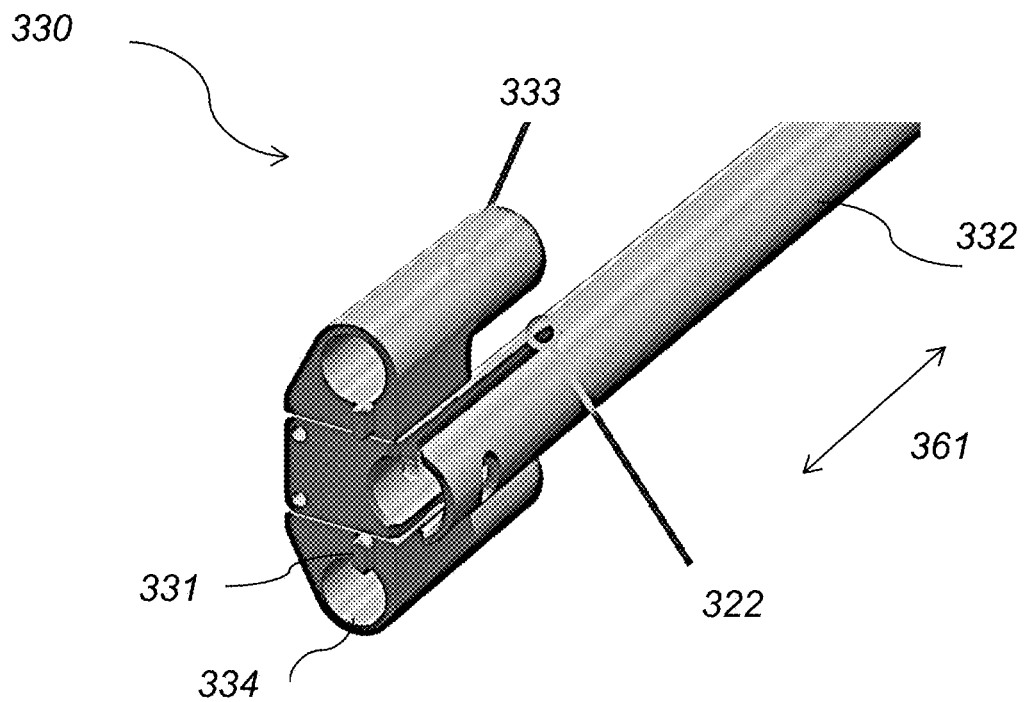
Figure 10E:
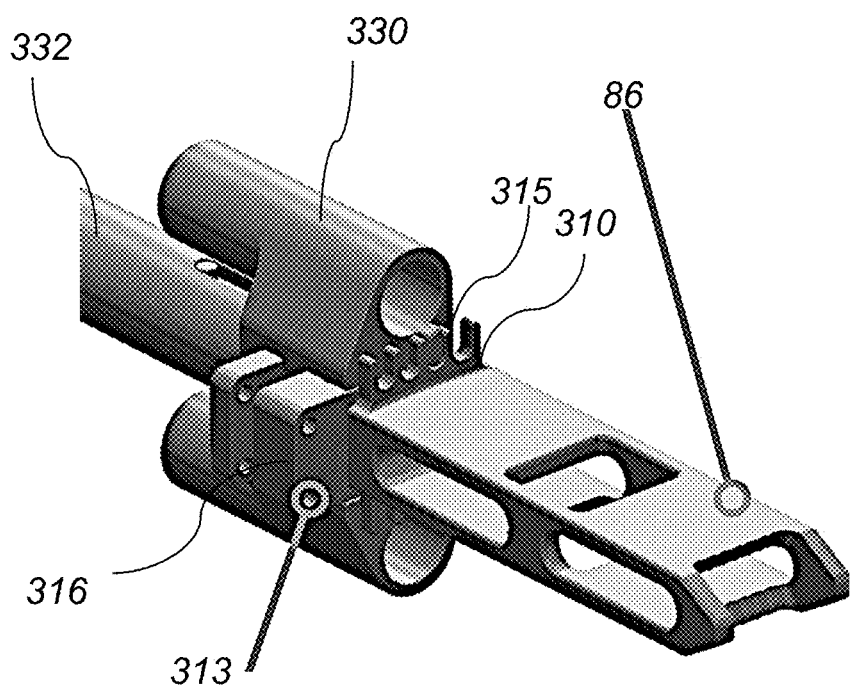
Figure 10F:
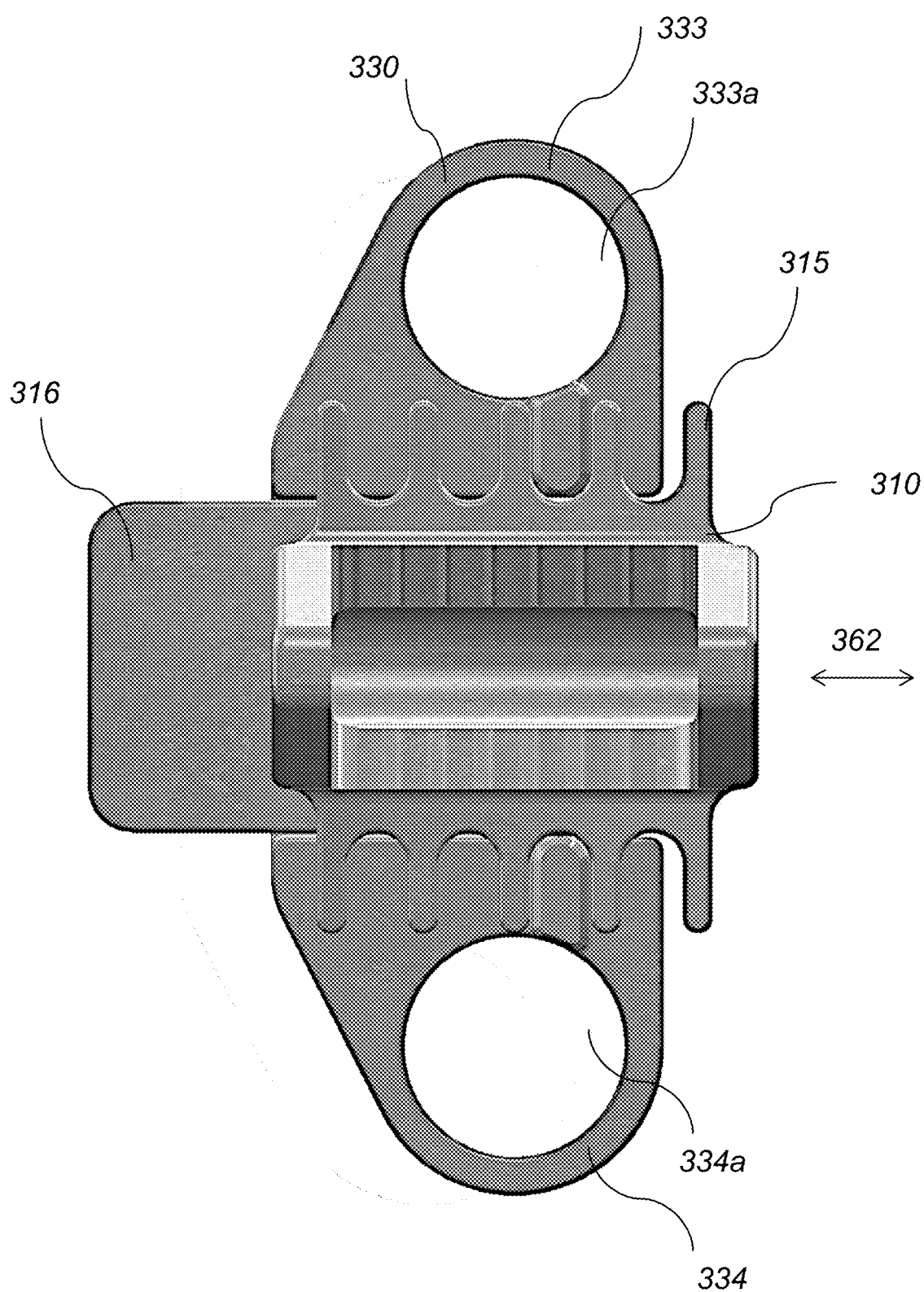

Referring to FIG. 10A to FIG. 10F, a centering broach tool 300 includes an elongated shaft 320, and a broach 86. Broach 310 is attached at the distal end of the elongated shaft 320. The elongated shaft 320 includes a connect feature 306 at the proximal end, and alignment pins 302a, 302b, shown in FIG. 10B. In one example, connect feature 306 has square profile. In other examples, connect feature 306 has a cylindrical, spherical, or polygonal profile. Alignment pins 302a, 302b on the elongated shaft 320 are used to establish the lateral center of the insertion site. Broach 86 includes an elongated parallelepiped with a triangular shaped cutting front and a stop endplate 310. Stop endplate 310 includes fingers 312 extending from the top and bottom surfaces, as shown in FIG. 10B. Fingers 312 are used for measuring the lateral center of the insertion site. A Steinmann pin guide tool 330 is slid over the elongated shaft 320, as shown in FIG. 10A. The Steinmann pin guide 330 includes an elongated tubular shaft 332, two connected tubular components 333, 334 having through openings 333a, 334a, respectively, and a stop plate 316. The elongated tubular shaft 332 extends along axis 361, is shaped and dimensioned to slide over the elongated shaft 320 of the broaching tool 300 and includes grip features 304 near the proximal end. In one example, grip features 304 include ridges and raised structures, as shown in FIG. 10A. Stop plate 316 extends from the distal end of the elongated tubular shaft 332 along a plane which is perpendicular to axis 361. The two connected tubular components 333 and 334 connect to the stop plate 316 by engaging a ball detent feature 335 with a corresponding feature of the stop plate 316. The Steinmann pin guide 330 is configured to slide along the longitudinal axis 361 of the elongated shaft 320, as shown in FIG. 10D and the two connected tubular components 333, 334 are configured to slide horizontally along axis 362, as shown in FIG. 10E. A locking tooth 331 formed in each of the connected tubular components 333, 334 is used for engaging the space between the fingers 315 of the stop endplate 310, as shown in FIG. 10E and FIG. 10F. In one example, the horizontal movement along axis 362 extends up to 6 mm from the lateral center and the horizontal movement increments are 3 mm. The horizontal movement increments are determined by the thickness of the stop fingers 315. Stop plate 316 includes pins 313 that are used to stop the horizontal translation of the two connected tubular components 333, 334.

Figure 11A:
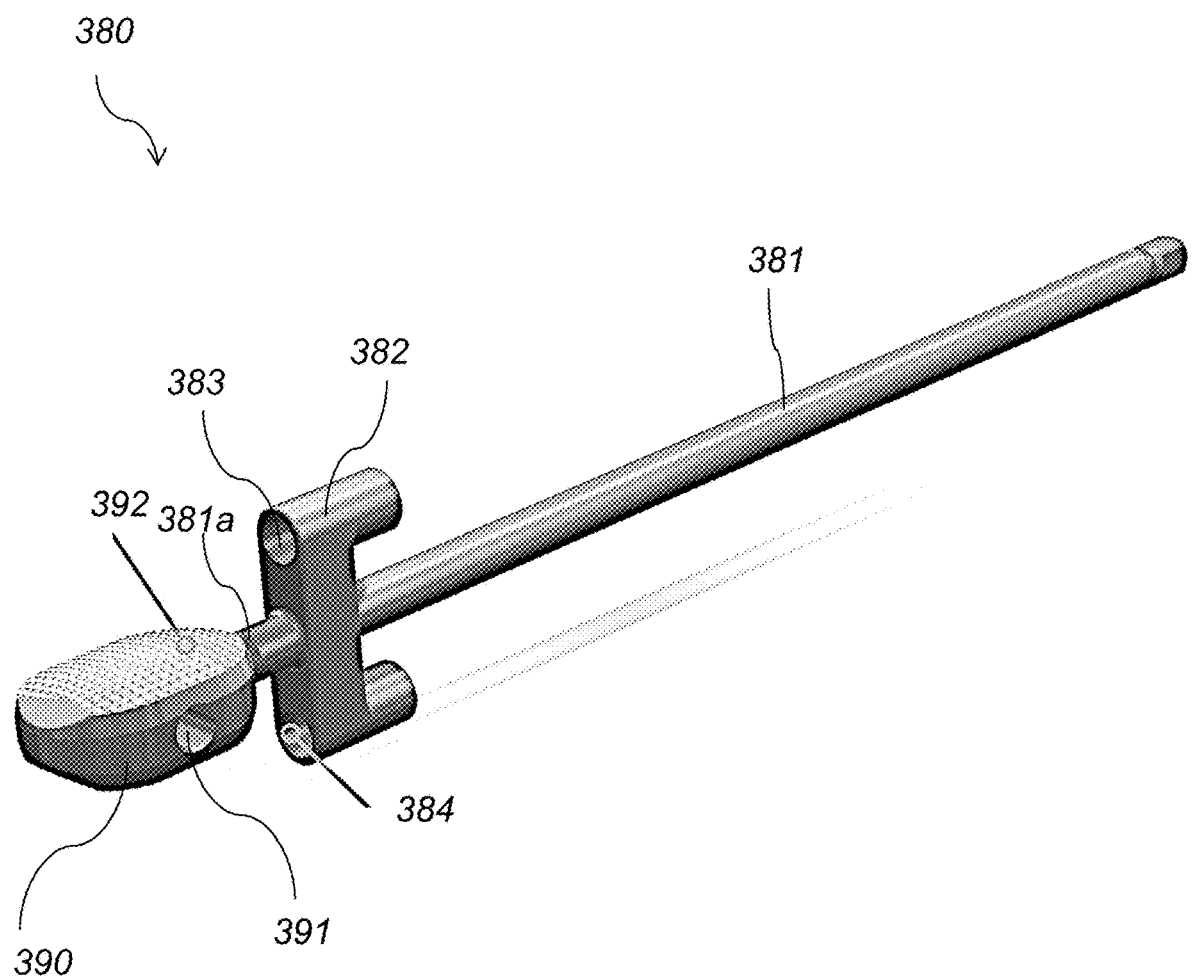
FIG. 11A to FIG. 11C depict a trial implant insertion tool used in the spinal disc replacement surgery via a lateral approach, according to this invention.
Figure 11B:
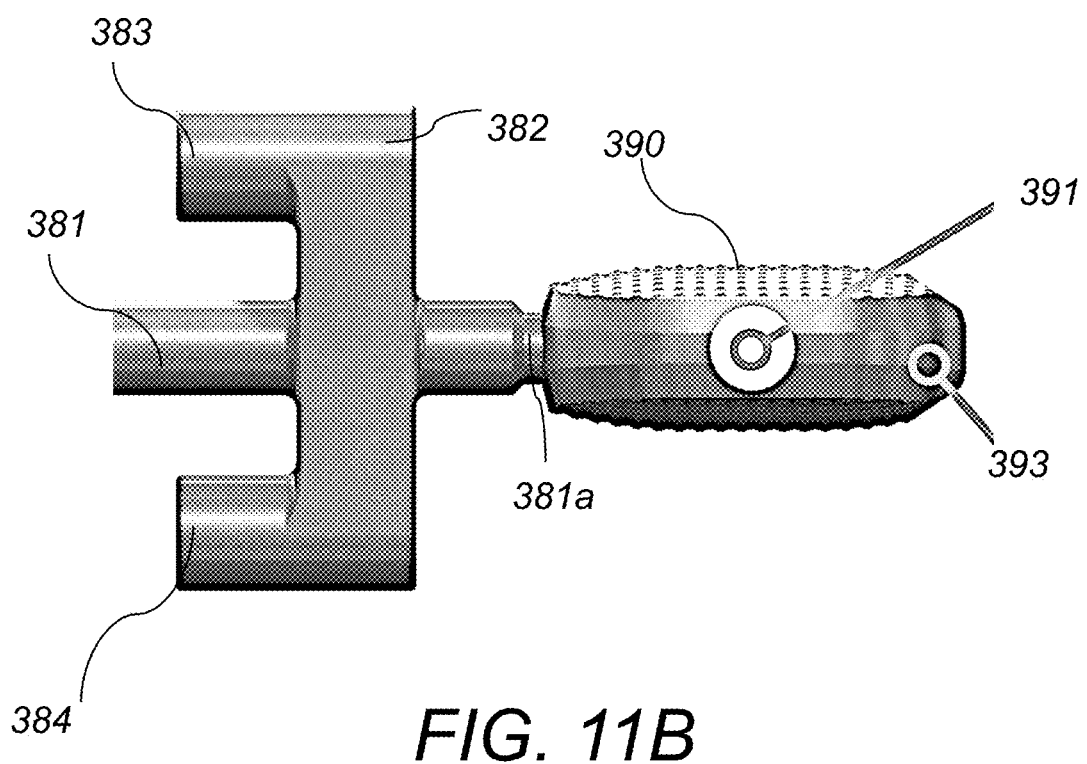
Figure 11C:
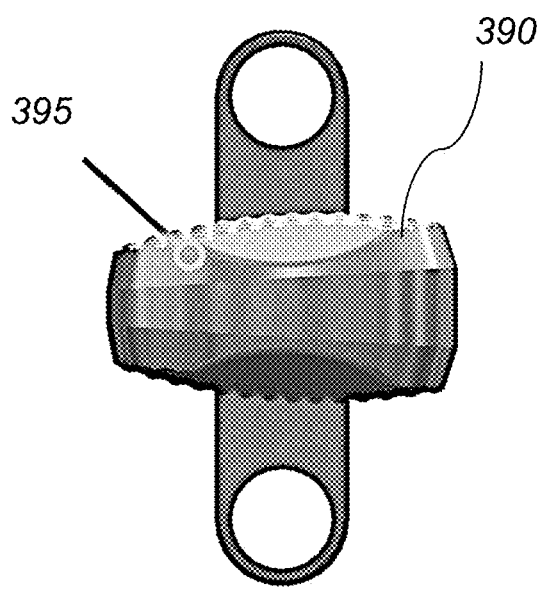
Figure 12A:
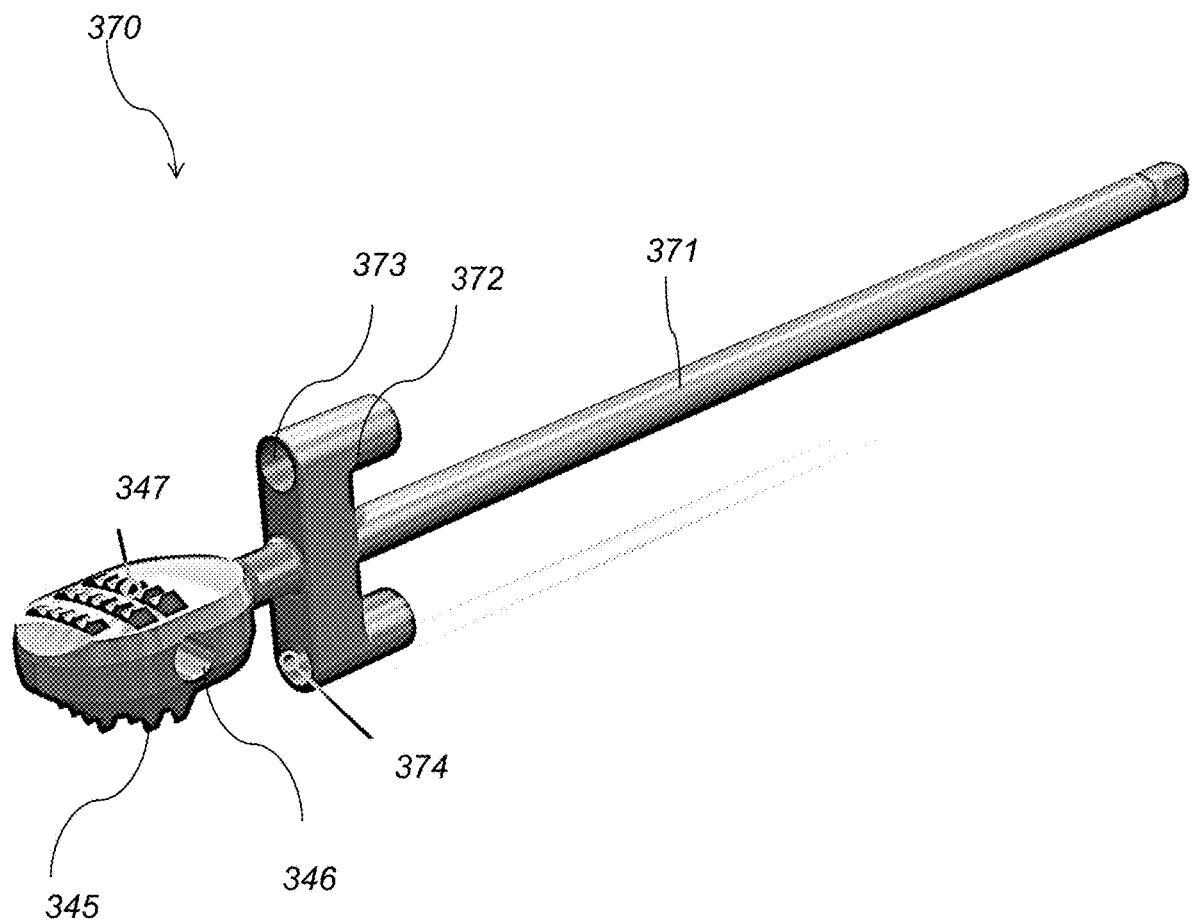
FIG. 12A to FIG. 12C depict a cutter insertion tool used in the spinal disc replacement surgery via a lateral approach, according to this invention.
Figure 12B:
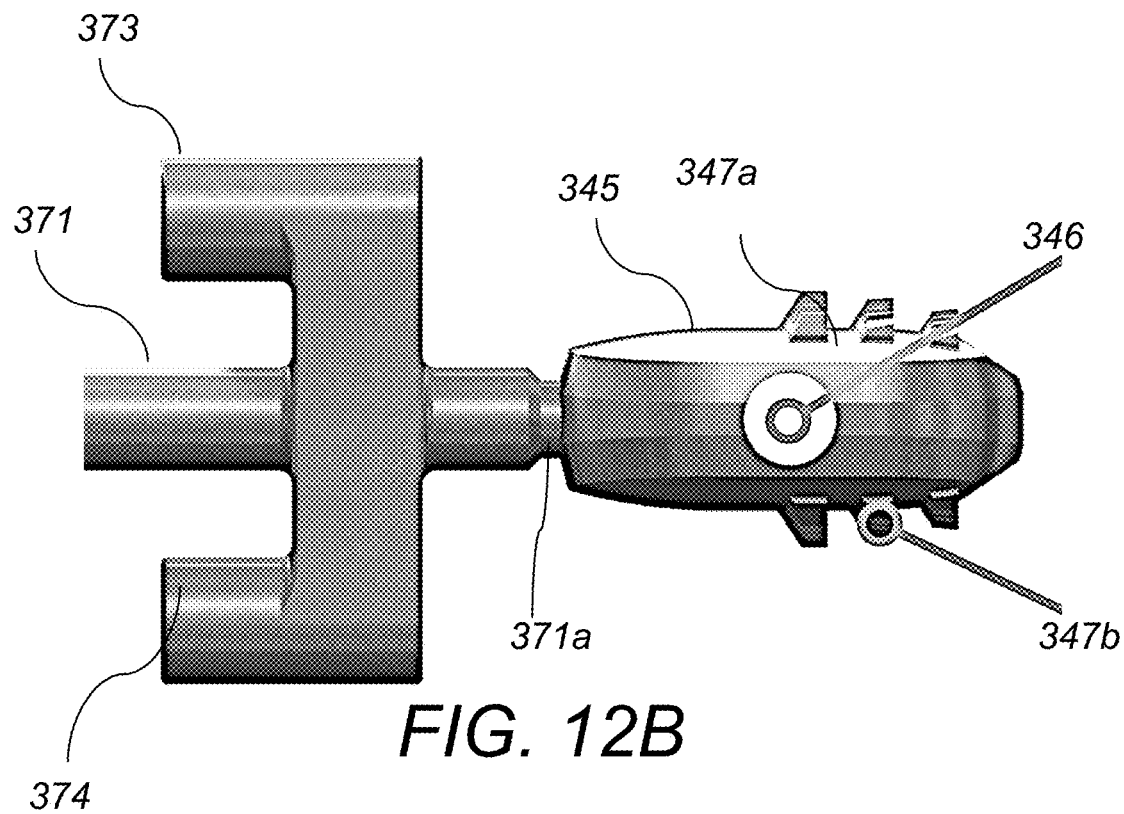
Figure 12C:
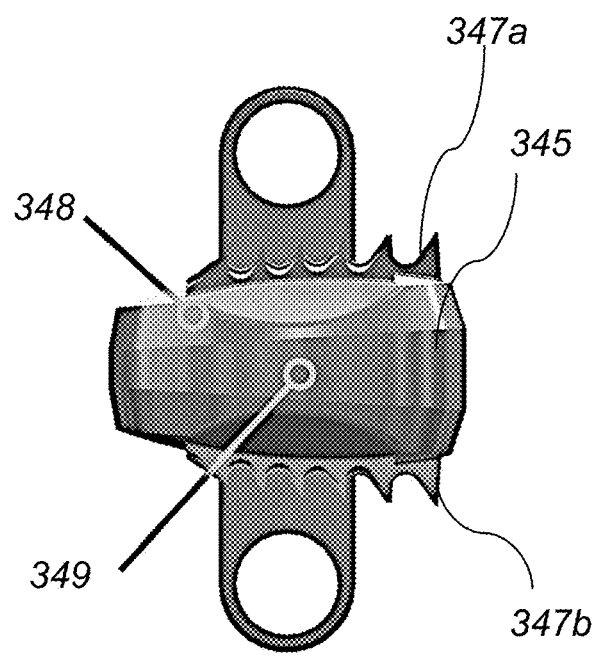

Referring to FIG. 11A to FIG. 11C, a trial implant insertion tool 380 includes an elongated shaft 381, and a Steinmann pin interface component 382. Elongated shaft 381 passes through a central opening of the Steinmann pin interface component 382 and is configured to have a trial implant 390 attached to its distal end 381a. The Steinmann pin interface component 382 includes two tubular components 382, 384 that are shaped and dimensioned to slide over the Steinmann pins 336a, 336b, respectively, as shown in FIG. 9J. Trial implant 390 includes an opening 391 in the side wall and has top and bottom surfaces 392 that are shaped and textured to match the shape and texture of the top and bottom surfaces of the actual implant 100. In the example of FIG. 12A-FIG. 12C, trial implant 390 has inclined top and bottom surfaces to match the lordosis of the actual implant 100, a bulleted nose 395 and top and bottom surfaces containing raised structures 392. Side opening 391 is used for alignment purposes.

Referring to FIG. 12A to FIG. 12C, a cutter insertion tool 370 includes an elongated shaft 371, and a Steinmann pin interface component 372. Elongated shaft 371 passes through a central opening of the Steinmann pin interface component 372 and is configured to have a cutter 345 attached to its distal end 371a. The Steinmann pin interface component 372 includes two tubular components 372, 374 that are shaped and dimensioned to slide over the Steinmann pins 336a, 336b, respectively, as shown in FIG. 9L. Cutter 345 includes an opening 346 in a sidewall and has top and bottom surfaces 347a, 347b that are shaped to match the tooth profile of the top and bottom surfaces of the actual implant 100. In the example of FIG. 12A-FIG. 12C, cutter 345 has inclined top and bottom surfaces 347a, 347b to match the lordosis of the actual implant 100, a bulleted nose 349 and top and bottom surfaces containing teeth 347. Side opening 346 is used for alignment purposes.

Several embodiments of the present invention have been described. Nevertheless, it will be understood that various modifications may be made without departing from the spirit and scope of the invention. Accordingly, other embodiments are within the scope of the following claims.

What is claimed is:

1. A method for spinal disc replacement comprising:
   making an incision along a lateral direction of a patient's abdominal oblique muscles to access an intervertebral disc located between adjacent superior and inferior vertebras via a lateral approach;
   making an incision through an annulus fibrosis of the intervertebral disc and removing a nucleus pulposus of the intervertebral disc to generate an opened disc space;
   determining and selecting an appropriate sized and shaped implant for the opened disc space by inserting incremental trial implants into the opened disc space, wherein the trial implants comprise varying footprint sizes, wedge angle and height;
   determining a trial implant depth so that in anterior-posterior X-ray imaging views first and second reference circles on first and second sides of the trial implants are aligned, respectively;
   generating first and second openings located on the superior and inferior vertebras, respectively, by using a guide tool comprising a rod and a plate mounted at a distal end of the rod and wherein the plate comprises first and second reference openings, and drilling into the superior and inferior vertebras through the first and second reference openings and wherein the first and second openings comprise depths selected based on the patient's anatomy;
   inserting first and second Steinmann pins into the first and second openings, respectively;
   inserting a tooth profile cutter in the opened disc space between the first and second Steinmann pins by mounting the tooth profile cutter to the plate of the guide tool and inserting the first and second reference openings of the plate over the first and second Steinmann pins and then cutting first and second tooth profiles in the inferior and superior surfaces of the superior and inferior vertebras, respectively, and wherein the first and second tooth profiles correspond to tooth profiles on top and bottom surfaces of a selected implant, respectively;
   removing the tooth profile cutter from the opened disc space and inserting the selected implant in the disc space between the first and second Steinmann pins by mounting the selected implant to the plate of the guide tool and inserting the first and second reference openings of the plate over the first and second Steinmann pins.

2. The method of claim 1, further comprising placing the patient in a lateral decubitus position on an operating table prior to making the incision.

3. The method of claim 1, further comprising using a rasp to prepare an inferior endplate of the superior vertebra and a superior endplate of the inferior vertebra.

4. The method of claim 1, further comprising removing any bone spurs or osteophytes from the opened disc space and the inferior endplate of the superior vertebra and the superior endplate of the inferior vertebra.

5. The method of claim 1, wherein the tooth profile cutter is inserted at a depth determined so that in anterior-posterior X-ray imaging views first and second reference circles on first and second sides of the tooth profile cutter are aligned, respectively.

6. The method of claim 1, further comprising passing an inserter over the first and second Steinmann pins, securing the inserter to the Steinmann pins, connecting the selected implant to an advancing section of the inserter and inserting the selected implant into the opened disc space by advancing the advancing section of the inserter.

7. The method of claim 1, further comprising distracting the opened disc space equally bilaterally with a parallel distractor tool.

8. The method of claim 1, wherein the tooth profile cutter comprises a half rail cutter.

9. The method of claim 8, wherein after inserting the half rail cutter into the opened disc space, removing the half rail cutter and inserting a full rail cutter that corresponds to the half rail cutter.

10. A method for spinal disc replacement comprising:
   making an incision along a lateral direction of a patient's abdominal oblique muscles to access an intervertebral disc located between adjacent superior and inferior vertebras via a lateral approach;
   making an incision through an annulus fibrosis of the intervertebral disc and removing a nucleus pulposus of the intervertebral disc to generate an opened disc space;
   inserting a centering broach tool in the opened disc space, wherein the centering broach tool comprises an elongated shaft and a broach mounted at a distal end of the elongated shaft and wherein a proximal end of the broach comprises a stop endplate and the elongated shaft comprises first and second alignment pins that are used to establish a lateral center, and wherein the broach is entered in the opened disc space until the stop endplate stops against sides of the superior and inferior vertebras;

generating first and second openings located on the superior and inferior vertebras, respectively, by using a drill guide tool, wherein the drill guide tool comprises an elongated tubular component configured to slide over the elongated shaft of the broach and first and second tubular drill guides surrounding a distal end of the elongated tubular component and drilling into the superior and inferior vertebras through the first and second tubular drill guides and wherein the first and second openings comprise depths selected based on the patient's anatomy, as viewed under fluoroscopic imaging;

inserting first and second Steinmann pins into the first and second openings, respectively;

determining and selecting an appropriate sized and shaped implant for the opened disc space by inserting incremental trial implants into the opened disc space between the first and second Steinmann pins by mounting the trial implant to an end of the elongated tubular component of the drill guide tool and inserting the first and second tubular drill guides over the first and second Steinmann pins, wherein the trial implants comprise varying footprint sizes, wedge angle and height;

determining a trial implant depth so that in anterior-posterior X-ray imaging views an opening at a side of the trial implants is centered, respectively;

inserting a tooth profile cutter in the opened disc space between the first and second Steinmann pins by mounting the tooth profile cutter to an end of the elongated tubular component of the drill guide tool and inserting the first and second tubular drill guides over the first and second Steinmann pins and then cutting first and second tooth profiles in the inferior and superior surfaces of the superior and inferior vertebras, respectively, and wherein the first and second tooth profiles correspond to tooth profiles on top and bottom surfaces of a selected implant, respectively;

removing the tooth profile cutter from the opened disc space and inserting the selected implant in the disc space between the first and second Steinmann pins by mounting the selected implant to an end of the elongated tubular component of the drill guide tool and inserting the first and second tubular drill guides over the first and second Steinmann pins.

* * * * *